US007699813B2

(12) United States Patent
Liversidge

(10) Patent No.: US 7,699,813 B2
(45) Date of Patent: Apr. 20, 2010

(54) MEDICAL NEEDLE ASSEMBLIES

(75) Inventor: Barry Peter Liversidge, The Wick, Wick Road, Langham, Colchester, Essex (GB) CO4 5PE

(73) Assignee: Barry Peter Liversidge, Colchester, Essex (GB)

( * ) Notice: Subject to any disclaimer, the term of this patent is extended or adjusted under 35 U.S.C. 154(b) by 1079 days.

(21) Appl. No.: 10/518,950

(22) PCT Filed: Jun. 23, 2003

(86) PCT No.: PCT/GB03/02689
§ 371 (c)(1),
(2), (4) Date: Jun. 29, 2005

(87) PCT Pub. No.: WO04/000397
PCT Pub. Date: Dec. 31, 2003

(65) Prior Publication Data
US 2005/0277893 A1    Dec. 15, 2005

(30) Foreign Application Priority Data
Jun. 22, 2002    (GB)    .................................. 0214452.5
Feb. 3, 2003    (GB)    .................................. 0302393.4

(51) Int. Cl.
*A61M 5/00*    (2006.01)
*A61M 5/32*    (2006.01)
(52) U.S. Cl. ......................... 604/198; 604/110; 604/194
(58) Field of Classification Search ................. 604/110, 604/192–198, 263
See application file for complete search history.

(56) References Cited
U.S. PATENT DOCUMENTS
4,894,055 A * 1/1990 Sudnak ....................... 604/198

| 4,955,866 A * | 9/1990 | Corey .......................... 604/192 |
| 5,013,305 A | 5/1991 | Opie et al. |
| 5,195,983 A | 3/1993 | Boese |
| 5,658,259 A * | 8/1997 | Pearson et al. .............. 604/232 |
| 5,795,336 A * | 8/1998 | Romano et al. ............. 604/192 |
| 6,773,415 B2 * | 8/2004 | Heiniger ..................... 604/110 |

FOREIGN PATENT DOCUMENTS
WO    WO 91/11212    8/1991

\* cited by examiner

*Primary Examiner*—Kevin C Sirmons
*Assistant Examiner*—Andrew M Gilbert
(74) *Attorney, Agent, or Firm*—Andrus, Sceales, Starke & Sawall, LLP

(57) ABSTRACT

A safety arrangement for a medical needle (15) has a support (14) for carrying the mount end of the needle, and a sleeve (16) slidably mounted on the support (14) for movement from an initial position to a retracted position and then back to a protecting position where the sleeve (16) covers the tip (21) of the needle (15). A spring (32) urges the sleeve toward its protecting position and a blocking member (23) projects forwardly from the support (14) and is movable between non-blocking and blocking positions. In the non-blocking position the sleeve (16) is free to slide from its initial position to its retracted position. On movement of the sleeve to its protecting position, the blocking member (23) moves to lie between the support (14) and sleeve (16) to prevent subsequent movement of the sleeve away from its protecting position. A control mechanism (27) releases the blocking member (23) so that it may move from its non-blocking position to its blocking position, the mechanism (27) being controlled by movement of the sleeve (16) from its initial position at least partway towards its retracted position.

34 Claims, 26 Drawing Sheets

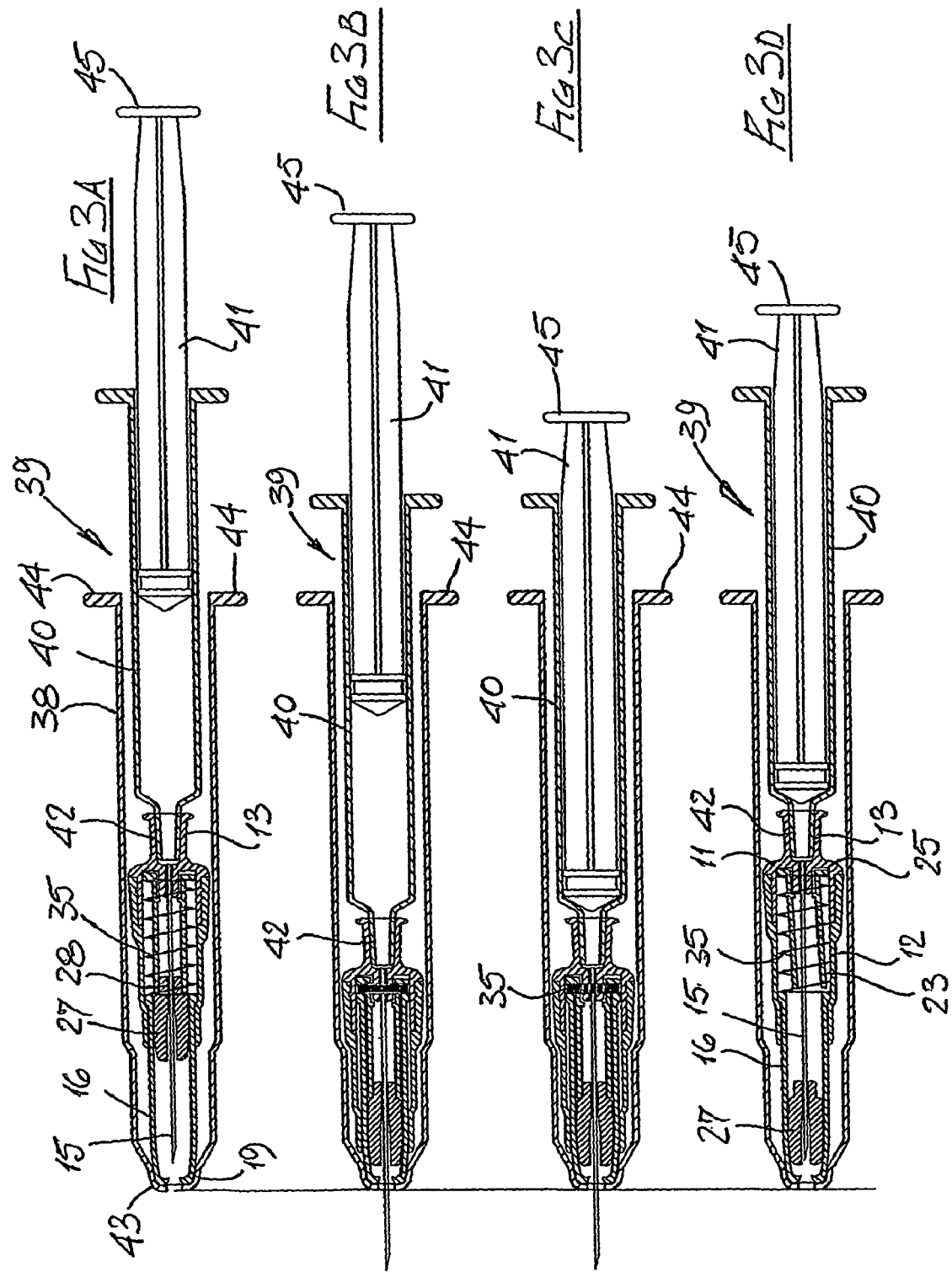

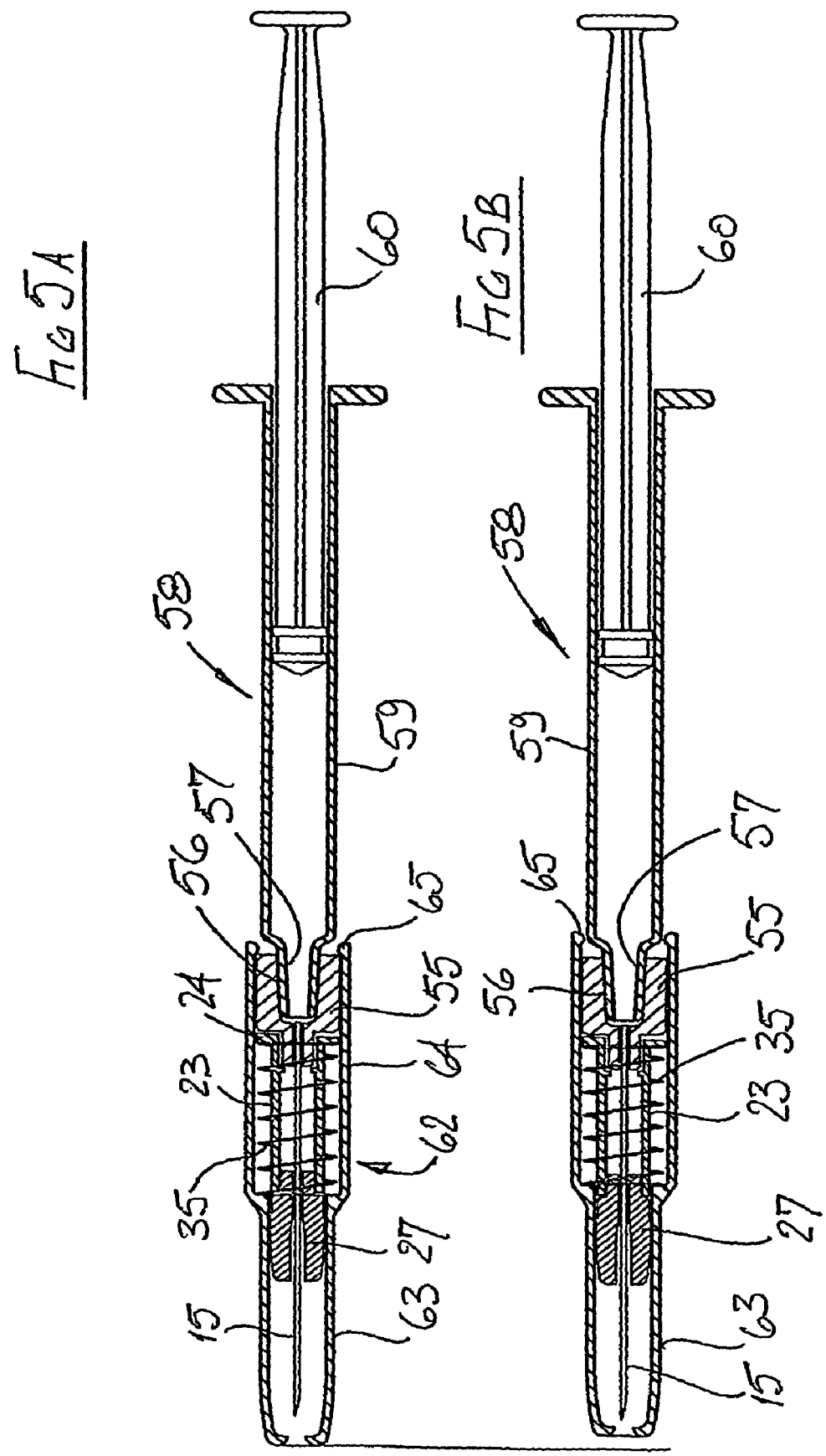

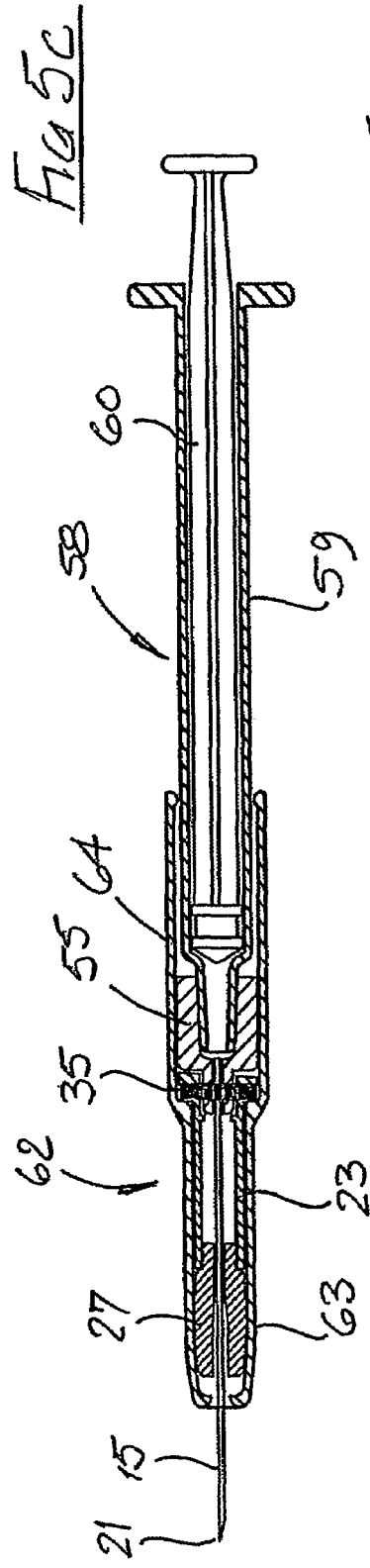
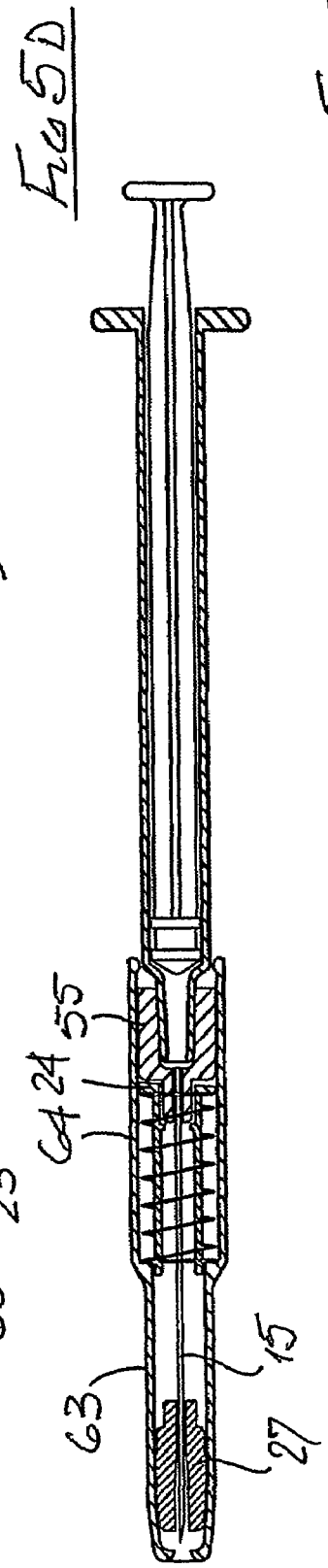
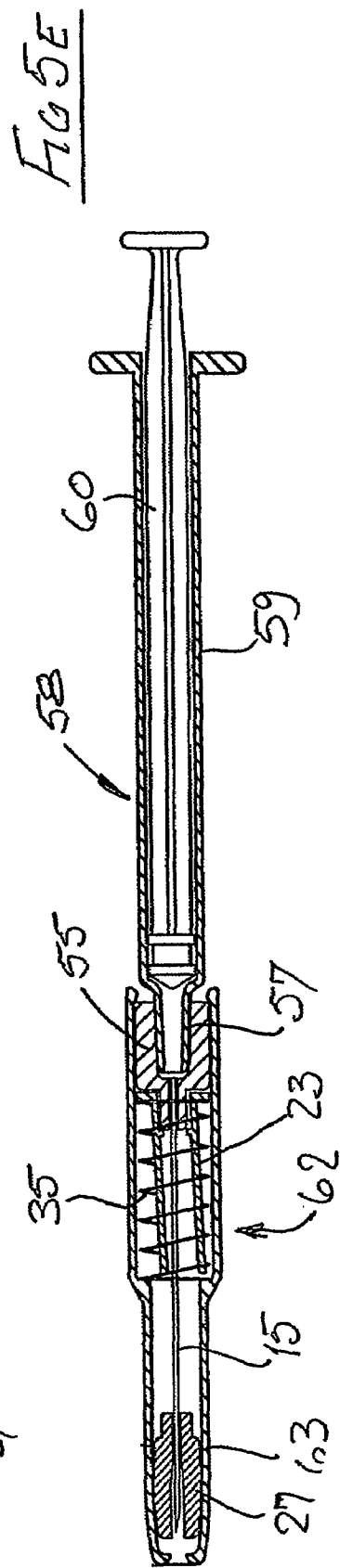

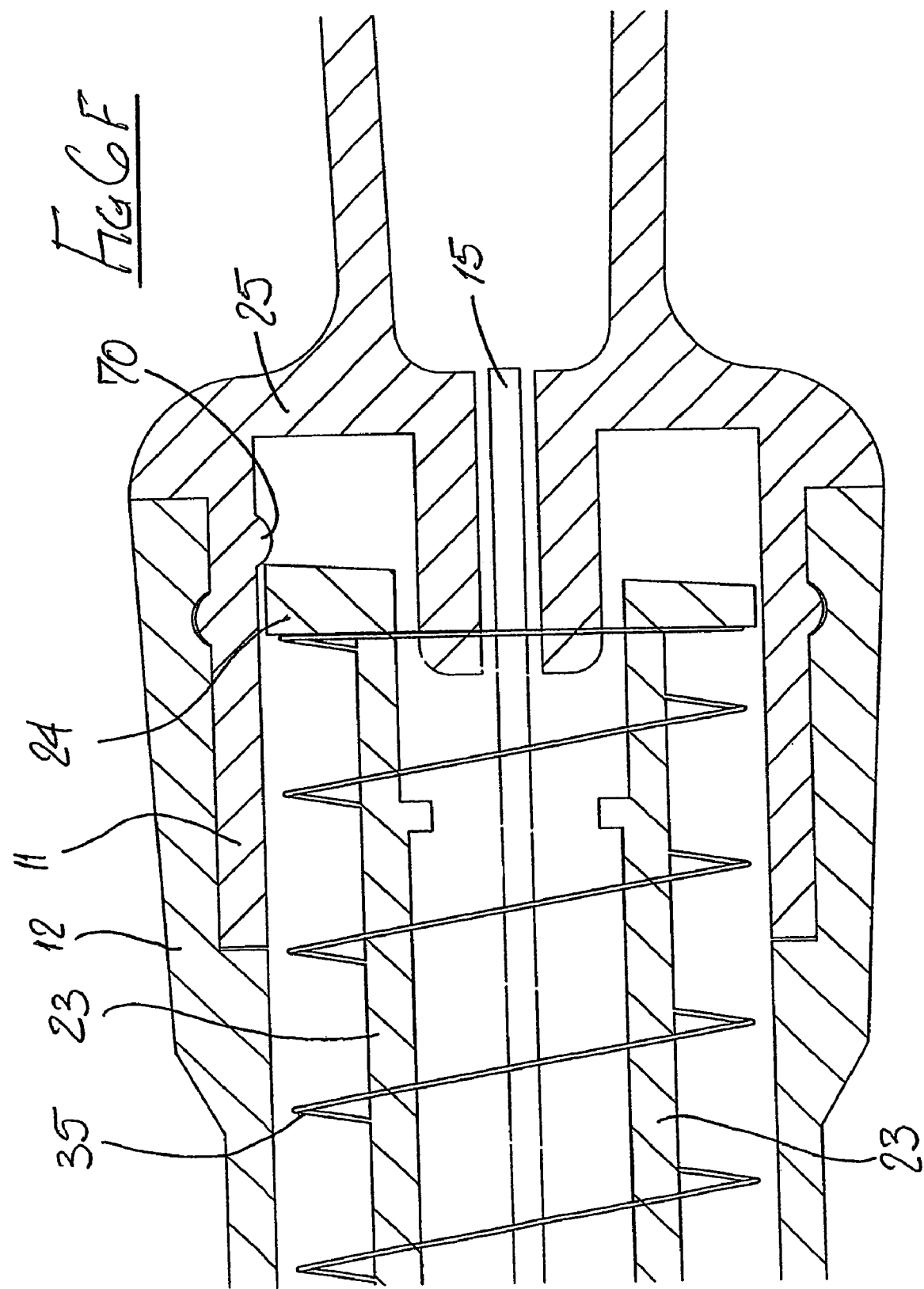

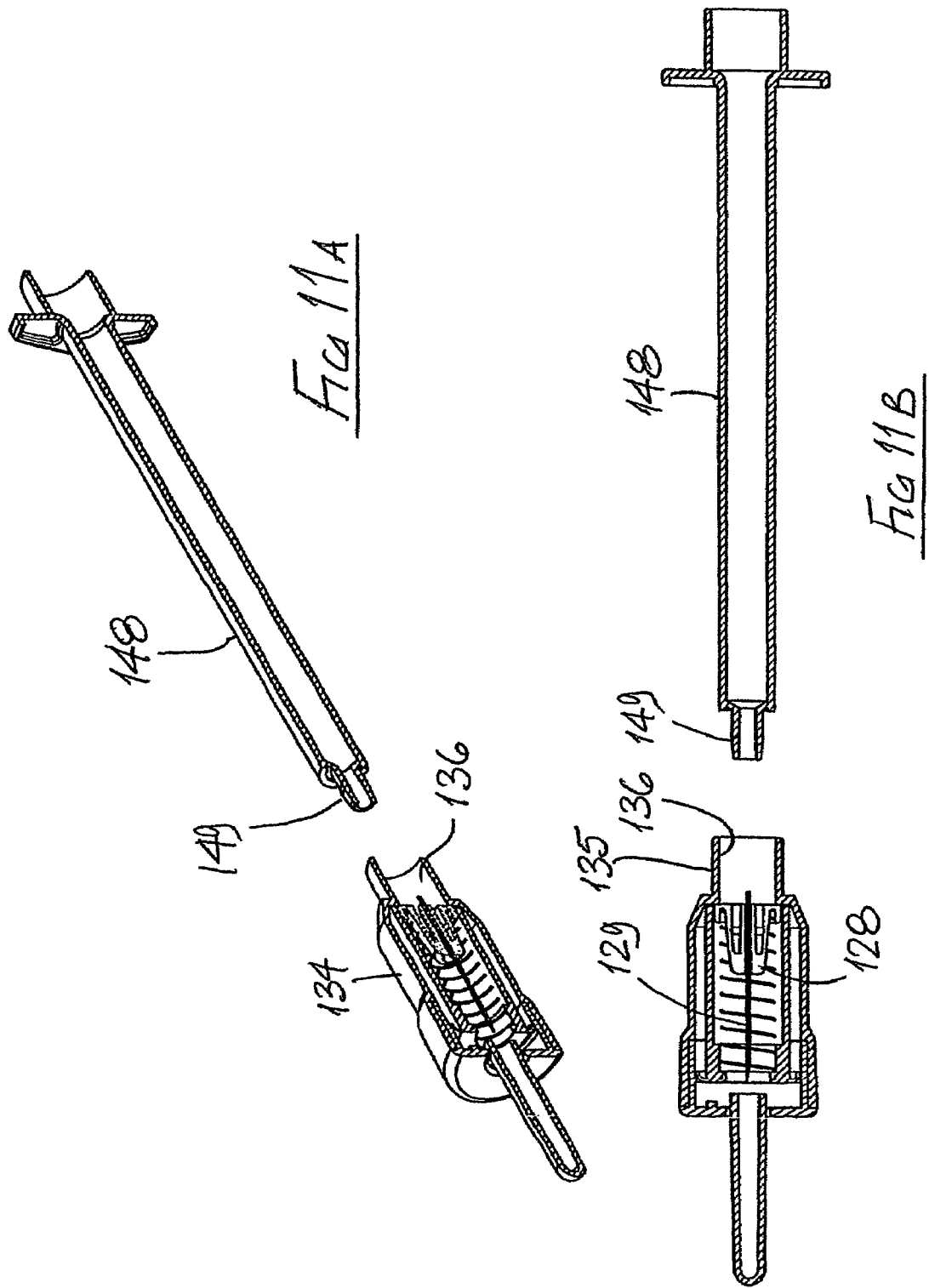

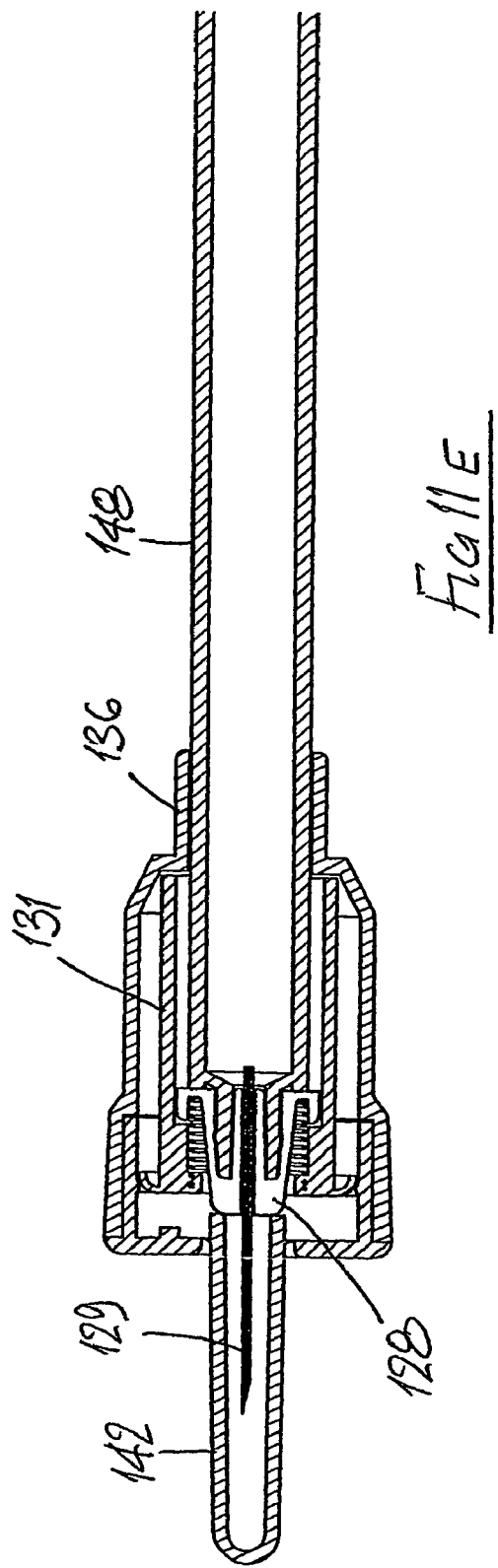
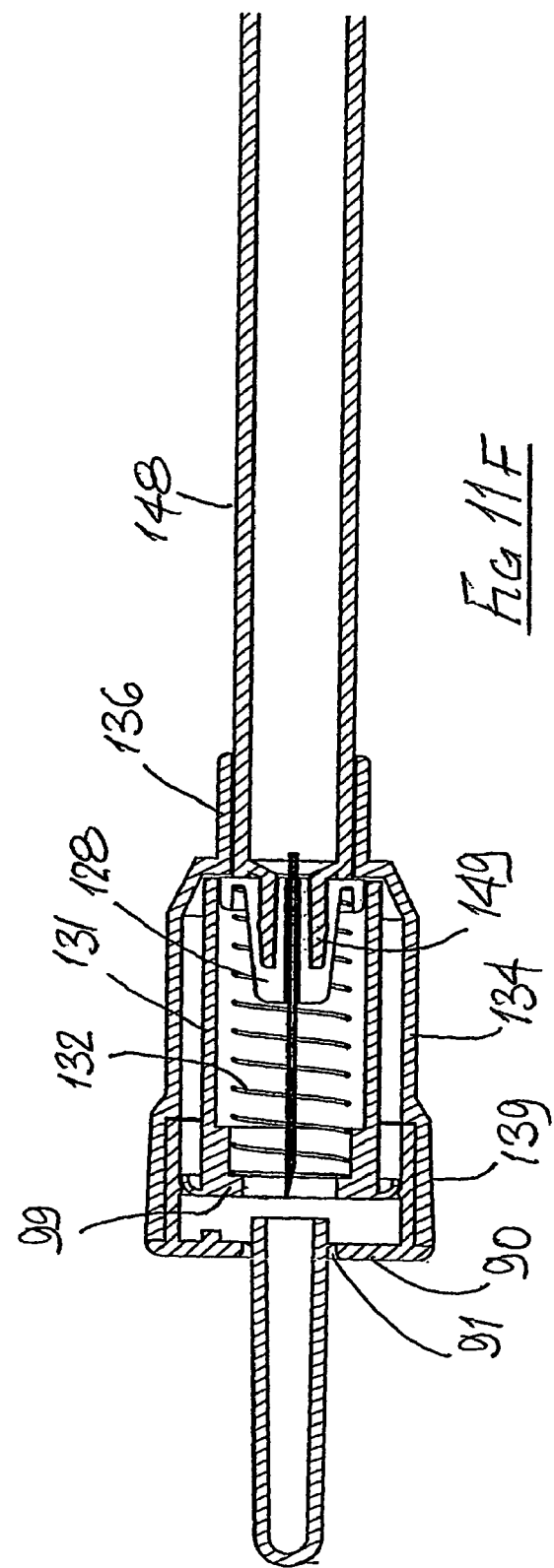

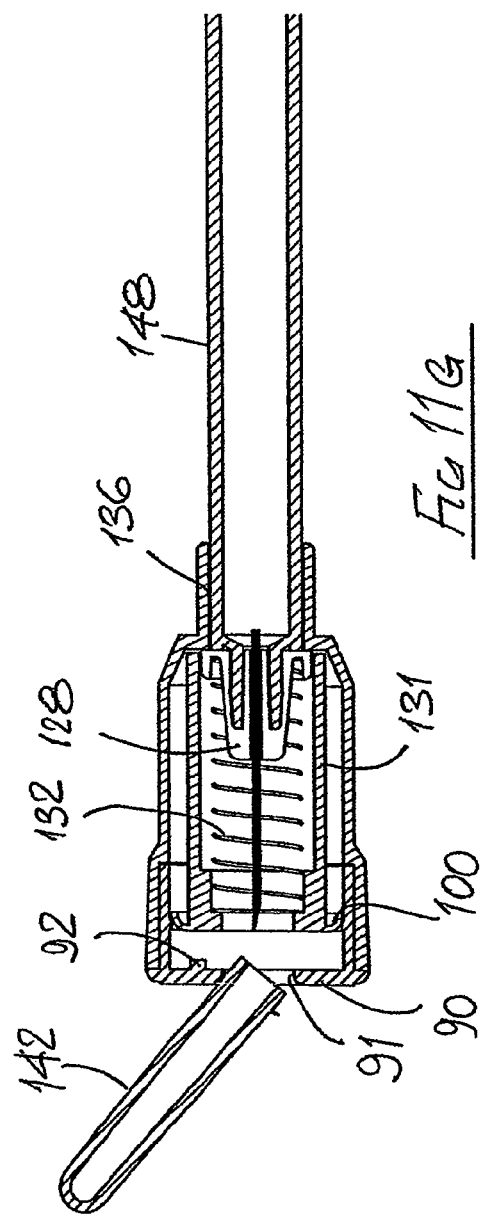
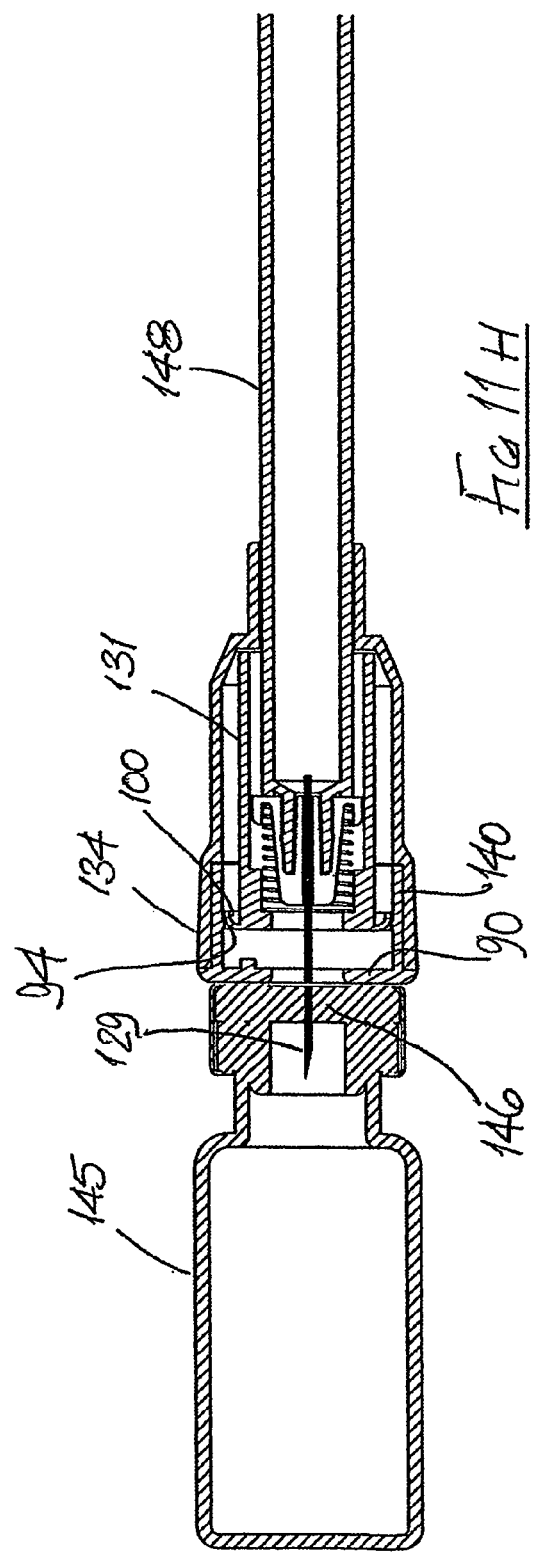

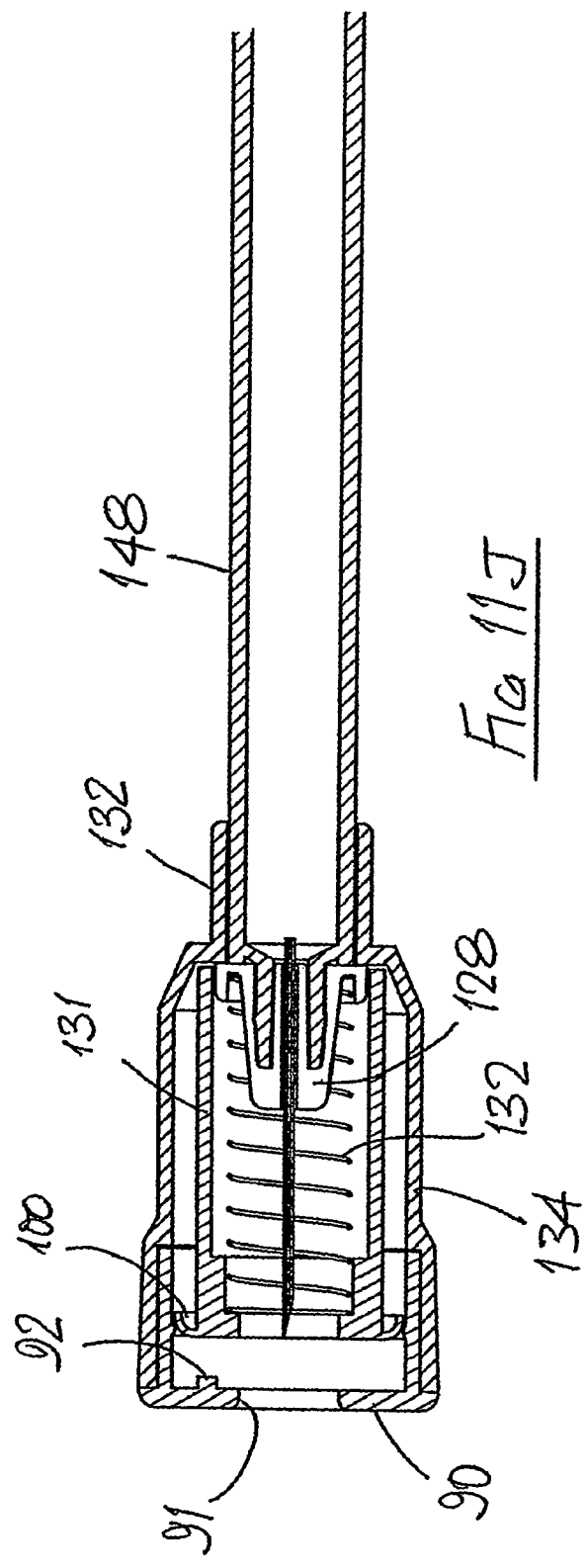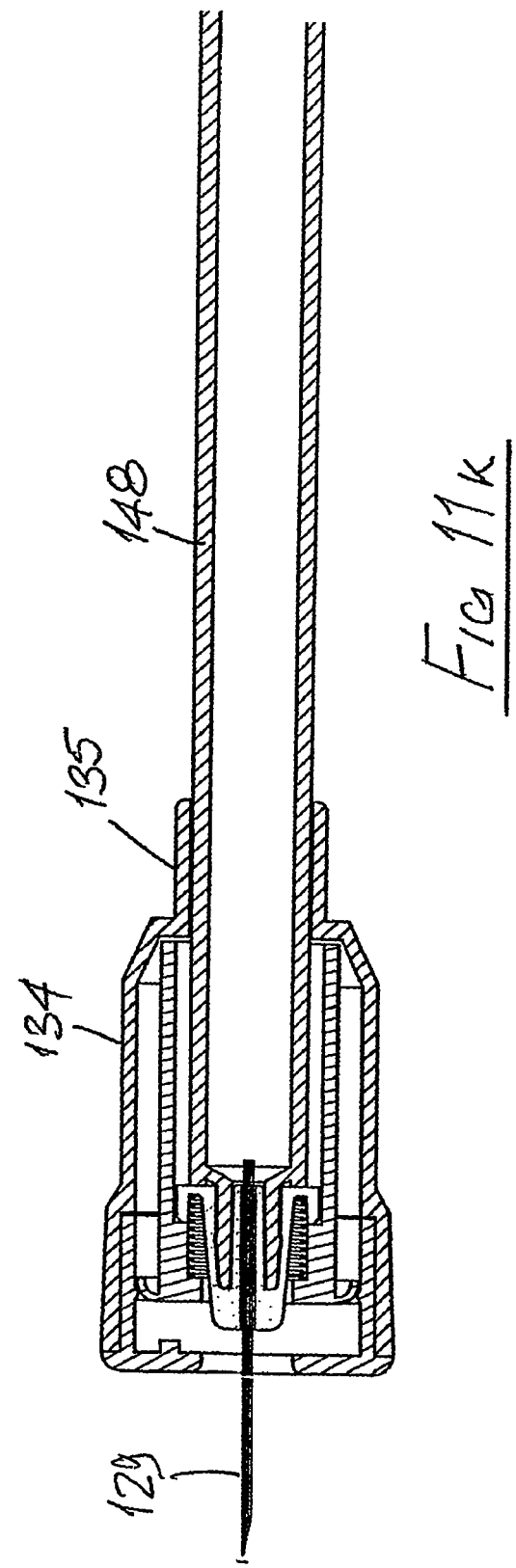

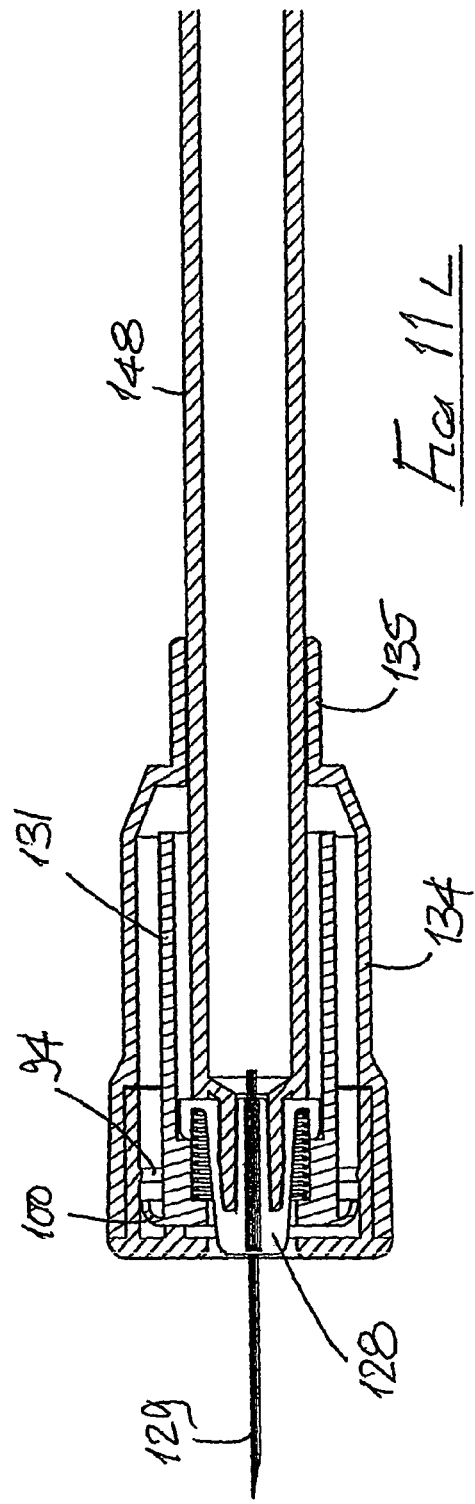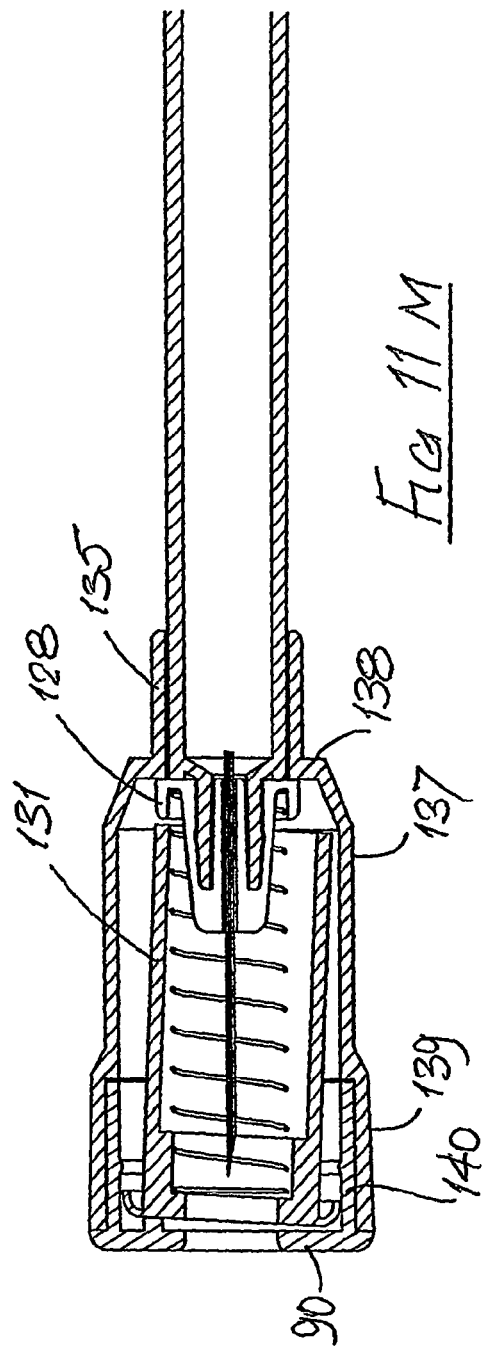

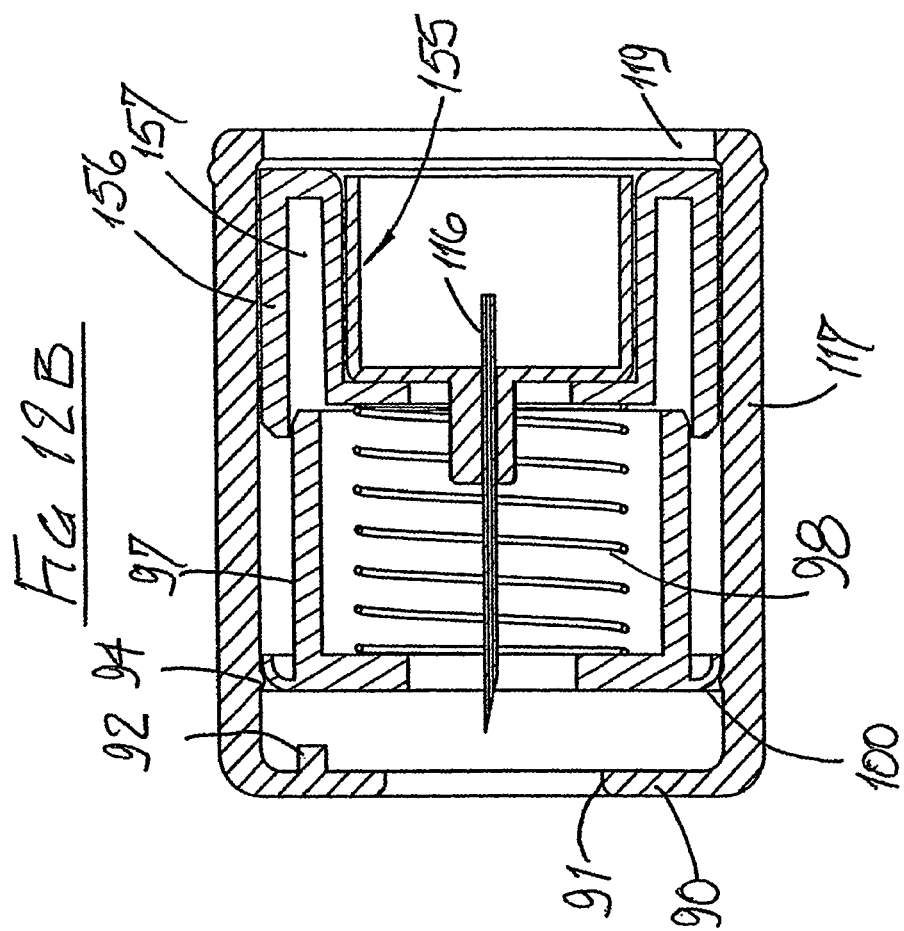
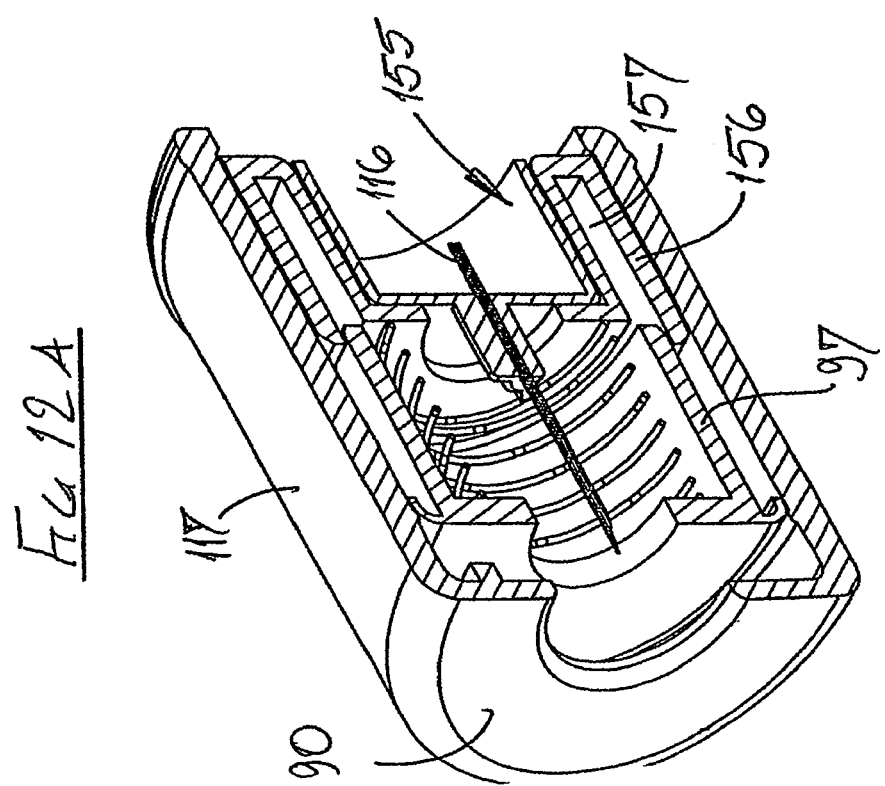

MEDICAL NEEDLE ASSEMBLIES

CROSS-REFERENCE TO RELATED APPLICATIONS

This application is the U.S. national stage application of International Application PCT/GB03/002689, filed Jun. 23, 2003, which international application was published on Dec. 31, 2003, as International Publication WO 2004/000397 in the English language. The International Application claims priority of Great Britain Patent Application No. 02 14452.5 filed Jun. 22, 2002 and Great Britain Patent Application No. 03 02393.4 filed Feb. 3, 2003.

This invention relates to a safety arrangement for a medical needle having a mount end and a sharp tip, intended for penetration of a human or animal body, or for other medical uses such as the penetration of a pierceable membrane of an intravenous medication system. The invention further relates to a safety arrangement including a medical needle as aforesaid, ready for use. For convenience, in the following all such medical uses will be described simply as the penetration of a body, even though specific embodiments may be intended for other medical uses.

Fluids of various kinds may be administered to a human or animal body by means of a hollow needle in conjunction with a source of the required fluid. For example, such a needle may be used in conjunction with a syringe holding a liquid drug, the needle being used to penetrate the body at the site at which the drug is to be received. Equally, body fluids may be withdrawn by using a hollow needle which is used to penetrate the body until the tip is located at the site from which fluid is to be withdrawn.

A recognised hazard for clinicians and other persons using medical needles for the above described purposes is the risk of a so-called needle-stick injury—that is to say the accidental penetration of the clinician's skin by the needle. Prior to the use of the needle to supply a fluid to or to withdraw fluid from a body, this rarely presents much of a problem, though once the needle has been used on a body, there is a very much higher risk of a serious consequence for the clinician. During use of the needle to penetrate the body tissues of a patient, the needle is likely to become contaminated with various organisms and should a needle-stick injury occur, these could infect the clinician.

There have been numerous proposals for protecting the sharp tip of a used needle, in order to reduce the risk of a needle-stick injury following use of the needle. Some proposals have actually increased the likelihood of such an injury by virtue of the action which must be performed to protect the tip, even if the risk thereafter is lessened. Despite all of the proposals which have previously been made, very few have achieved commercial success, nor has there been wide acceptance by the medical industry. Many proposals are somewhat complex and involve a significantly greater manufacturing cost, and so are unacceptable on economic grounds. Others are much more difficult to use as compared to an unprotected needle, and so are rejected by clinicians. Yet further proposals do not allow compliance with best practice protocols.

There is a significant demand for a protective device for use with a needle, and which allows a clinician to use the needle in much the same way as is done with an unprotected needle, but which can be manufactured economically and which provides a high degree of protection against needle-stick injury. In this connection, it is highly preferred that the device operates fully automatically, without intervention by the clinician, to give a degree of protection to the needle tip before use, and after use wholly prevents access to the needle tip other than by a determined attempt to override the protection. In this way, protection may be afforded not just to the clinician, but also to others who could come into a risky situation with used needles, such as waste disposal operators, cleaners, and so on.

A device which protects a needle tip without an operator having to perform any extra step on withdrawing the needle from a body is usually referred to as a passive protection device. This may be contrasted with an active protection device, where an operator is required to perform an extra step in order to protect a needle, following the withdrawal of the needle from a body. The requirement to perform an extra step leaves the needle unprotected for a longer period than with a passive protection device and further the performance of that extra step exposes the operator to a potentially hazardous situation, where needle-stick accidents can occur.

Consequent upon research and development, the present invention has evolved, to provide various forms of needle protection devices having enhanced characteristics, but all employing the same underlying passive protection concept.

Accordingly, this invention provides a safety arrangement for a medical needle having a mount end and a sharp tip, which arrangement comprises:

a support adapted directly or indirectly to carry the mount end of a needle so that the needle projects forwardly away therefrom;

a sleeve mounted directly or indirectly on the support and being slideable with respect thereto from an initial position where the sleeve covers at least the greater part of a carried needle to a retracted position where the tip of a carried needle and a part of the needle back from its tip is exposed, and then to a protecting position where the sleeve covers the needle tip and at least part of the needle back from its tip;

resilient means arranged to urge the sleeve towards its protecting position;

a blocking member at least a part of which projects forwardly from the support, the blocking member being movable between a non-blocking position where the blocking member extends generally parallel to the needle axis and the sleeve may slide to its retracted position and a blocking position where the blocking member has moved from its non-blocking position so as to be disposed between the support and a part of the sleeve, thereby blocking movement of the sleeve away from its protecting position; and control means which releases the blocking member for movement from its non-blocking position to its blocking position on movement of the sleeve away from its initial position towards its retracted position, so that on subsequent movement of the sleeve to its protecting position the blocking member will thereafter block movement of the sleeve away from its protecting position.

It will be appreciated that the safety arrangement of this invention may be provided with an integral medical needle, or may be adapted to receive a medical needle shortly before being used to undertake penetration of a body. Either way, a needle is initially protected at least to some extent, though preferably wholly, by the sleeve, which extends from the assembly support to overlie at least the greater part of the needle projecting from the support. The control member serves to hold the blocking member in such a position that the sleeve may be moved with light pressure on its tip to its retracted position, where that part of the needle projecting beyond the housing is exposed. Such pressure may be exerted by the skin of a patient or the pierceable membrane of a medical apparatus as a clinician pushes the needle into a body and so the movement of the sleeve to its retracted position requires no separate action by the clinician.

On withdrawing the needle from a body, the safety arrangement operates fully automatically and without the need for any operator intervention (i.e. it operates passively), to furnish a sleeve over the exposed part of a needle and to block that sleeve in a fully protecting position, from which the sleeve cannot be withdrawn short of destroying the safety arrangement. Thus, an operator is automatically and effectively protected against needle-stick injuries, following the completion of a medical procedure using the needle, when equipped with the safety arrangement.

The support may define a connector for a cylindrical body such as a syringe, to extend co-axially with the needle. In one embodiment, the cylindrical body may serve slidably to support the sleeve when the support has been connected to the body. Alternatively, the support may be defined by a rear wall of a tubular housing for the assembly and on or within which the sleeve is slidably carried.

The control means may include a releasable connection between two components which are relatively movable along the axis of a needle carried by the support, such that sufficient force releases the connection and then allows the blocking member to move to its blocking position, when the sleeve has moved to its protecting position. In a preferred embodiment, there is provided a control member mounted within the sleeve and the releasable connection is formed between the sleeve and the control member. In another embodiment, the releasable connection is formed between a housing for the assembly and the blocking member, movement of the sleeve towards its retracted position releasing that connection to permit the blocking member to move towards the support, thereafter to perform the blocking action on movement of the sleeve to its protecting position.

In a preferred form of this invention, the assembly includes a tubular housing having a rear wall which forms the needle support, the housing being open at its opposed end so that a supported needle may extend from the rear wall and project out of the opposed end. In such a case, the sleeve may be slidably mounted within the housing to surround a supported needle, the sleeve having a rear end nearer the rear wall of the housing and there being means to prevent the sleeve sliding off the housing.

For this embodiment, the blocking member may have a base disposed between the rear end of the sleeve and the rear wall of the housing and a blocking section which extends from the base generally parallel to the length of the sleeve and co-operable with the sleeve. A spring should be arranged to urge apart the sleeve and the blocking member. In this arrangement:
  with the sleeve in its initial position the control member is disposed adjacent the rear end of the sleeve, engaged with the blocking section of the blocking member;
  on movement of the sleeve to its retracted position the control member releasable connection is released so permitting the control member to move into the sleeve, the control member guiding the blocking section into the sleeve; and
  on the sleeve subsequently moving to its protecting position under the action of the spring, the base of the blocking member is urged to bear on the housing rear wall and the blocking section of the blocking member engages behind the rear end of the sleeve, so preventing subsequent retraction of the sleeve from its protecting position.

In a preferred form, the control means includes a control member which is located within the sleeve, when the sleeve is in its initial position. A releasable connection between the control member and the sleeve may comprise inter-engaged stops on both the outer surface of the control member and the internal surface of the sleeve, which stops will override each other on the application of sufficient axial force thereto. Alternatively, a simple frictional connection may be provided between the sleeve and the control member, whereby the control member will stay at any position within the sleeve unless a sufficient axial force is applied thereto.

In the former case, the spring may act between the control member and an internal flange formed within the tubular blocking member and so will act indirectly on the sleeve. In the latter case, the spring may be external to the blocking member and act directly on the sleeve.

Preferably, the sleeve is translucent and the control member is of a high visibility material. In this way, the control member can also act as a visual indicator so that a user may readily see whether the assembly has been used and so should be discarded, because the control member will be visible at the forward end of the sleeve. For an arrangement having a releasable connection with inter-engageable stops, there is the additional benefit of an audible "click" when the control member is moved forwardly by the spring.

In various preferred embodiments, the base of the blocking member is circular and has a central hole through which the needle projects. The rearwardly directed face of that base may lie at an angle of a few degrees to the true radial plane and is opposed to a surface of the support, which surface lies in the true radial plane. The spring is arranged to urge the blocking member rearwardly, but so long as the blocking member is constrained by the control member or the sleeve to lie co-axial with or extending parallel to the axis of the needle, said rearwardly directed face of the base will not lie flat against the radial surface of the support. Upon release of the blocking member, the spring urges the rearwardly directed face of the base to lie flat against the surface of the support, thus inclining the blocking member to the axis of the needle. The blocking member is thus able to perform its blocking function, to prevent the sleeve moving away from its protecting position.

This invention extends to an assembly of this invention as described above, in combination with a medical needle having a mount end and a tip, the mount end of the needle being carried by the support, to extend therefrom, through the blocking member and the sleeve.

Advantages possessed by various embodiments of the present invention are that they afford wholly aseptic operations, a pre-requisite concerning the introduction of a hollow-bore needle into a body. In preferred embodiments where the initial position and protecting position of the sleeve are the same, and so the needle tip is at all times covered other than when the needle is within a body, there is no possibility of the needle being touched accidentally, either by a clinician or by some other component. If the sleeve unintentionally touches some other body to an extent sufficient to expose the needle tip, return of the sleeve to its fully forward position will lock the sleeve, so preventing use of the needle to perform an injection.

Further, the conventional practice of un-sheathing of a needle by removing a cap is wholly eliminated. It is possible to damage a needle tip by removing a cap and such damage leads to a more painful injection.

As the needle is covered at all times, other than during body penetration, there is the further advantage of a placebo effect, in that a patient will not see, and so not be frightened by, the needle. Thus, it is possible to give injections even with highly needle-phobic patients.

By way of example only, several embodiments of this invention will now be described in detail, with reference to the accompanying drawings, showing the embodiments in various settings. In the drawings.

Figure 4A:
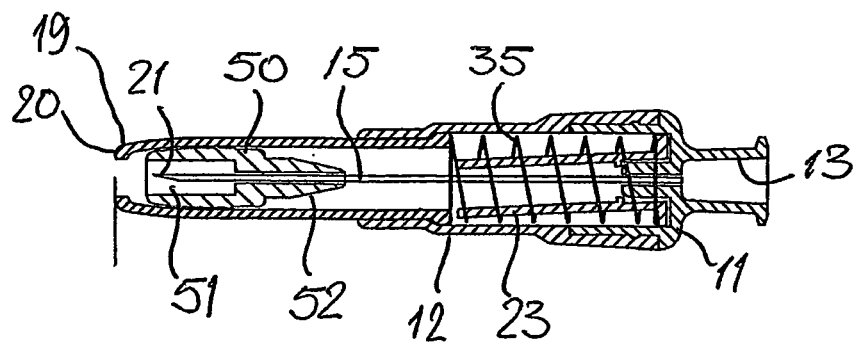
Figure 4B:
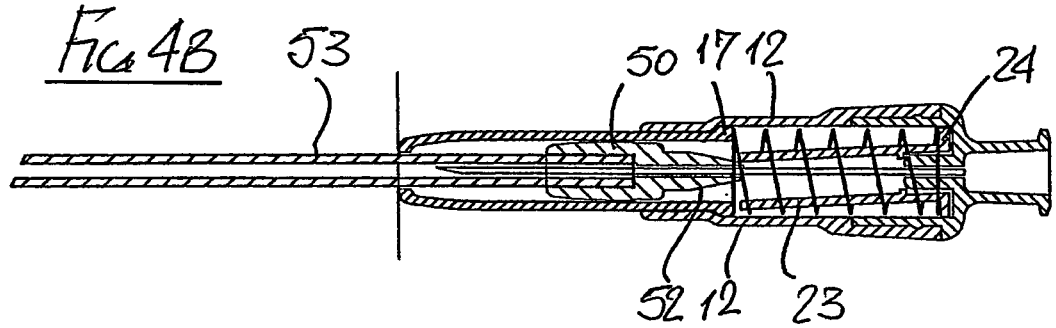
Figure 4C:
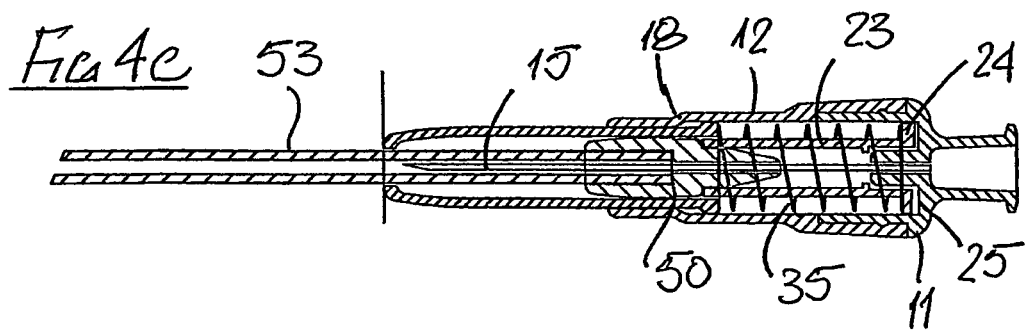
Figure 4D:
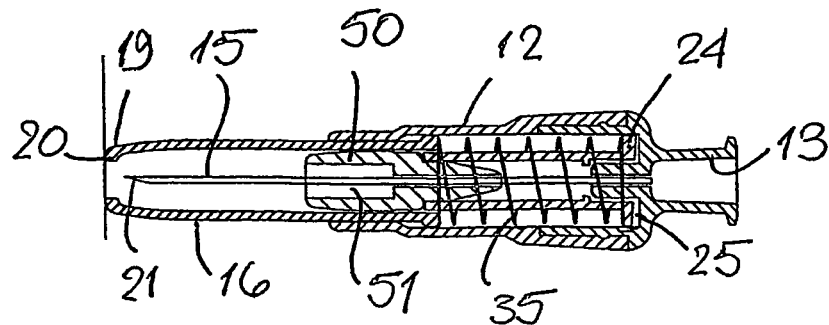
Figure 6A:
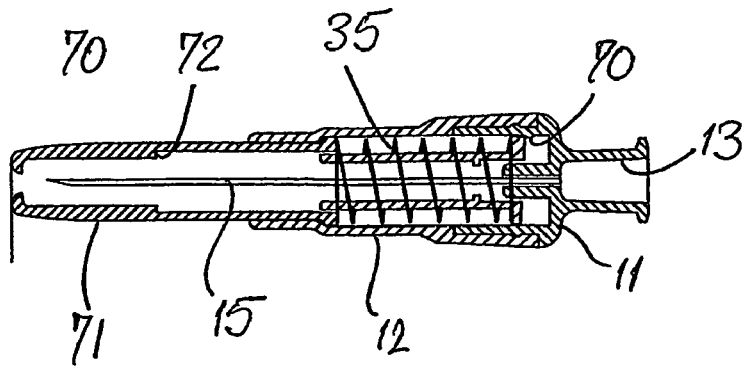
Figure 6B:
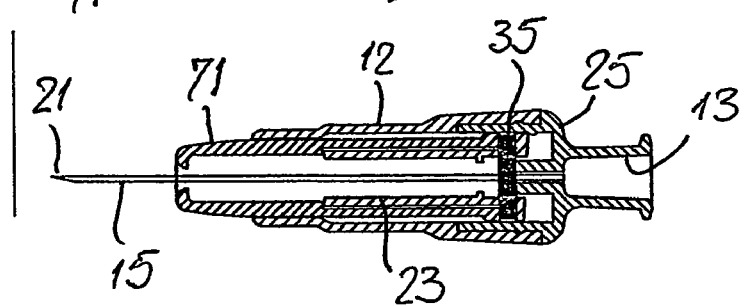
Figure 6C:
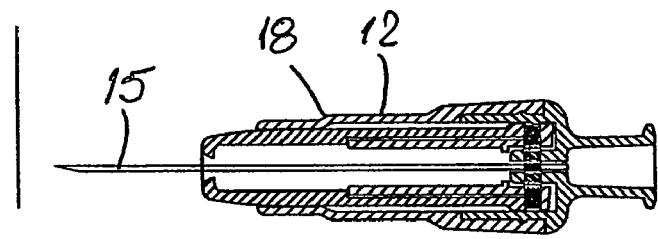
Figure 6D:
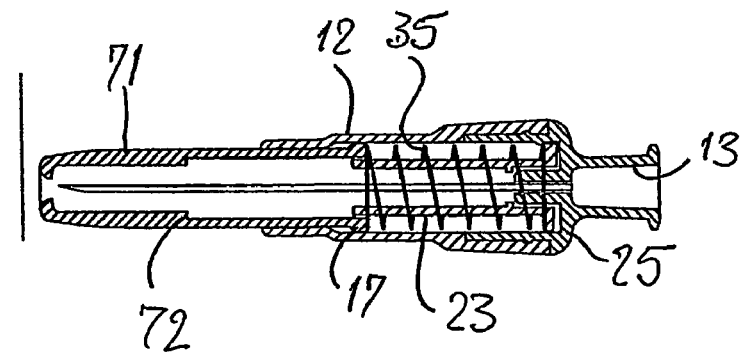
Figure 6E:
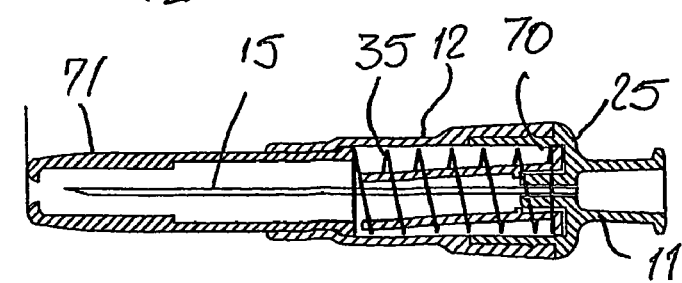
Figure 9A:
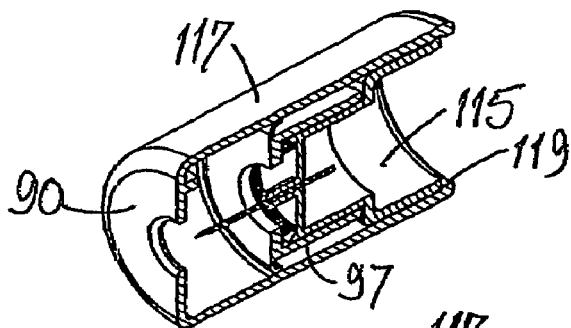
Figure 9B:
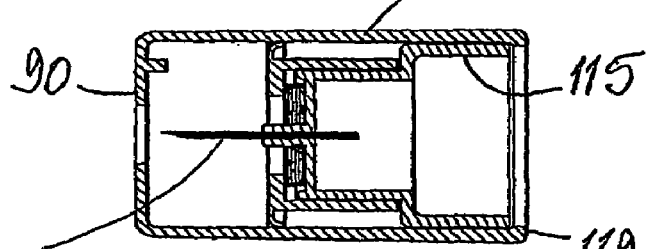
Figure 9C:
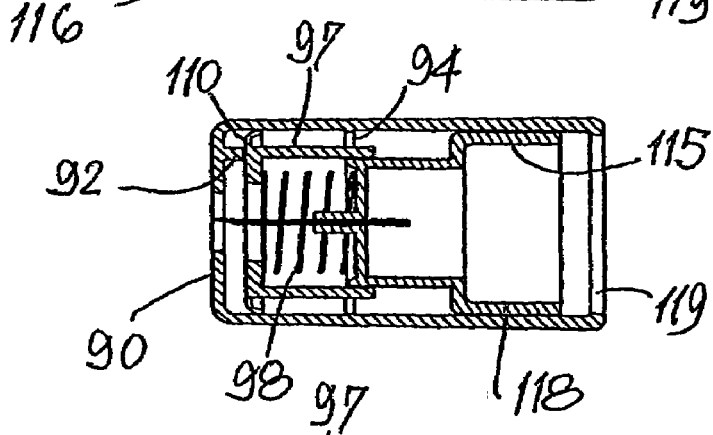
Figure 9D:
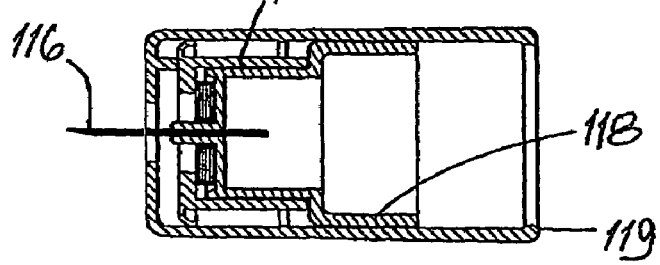
Figure 9E:
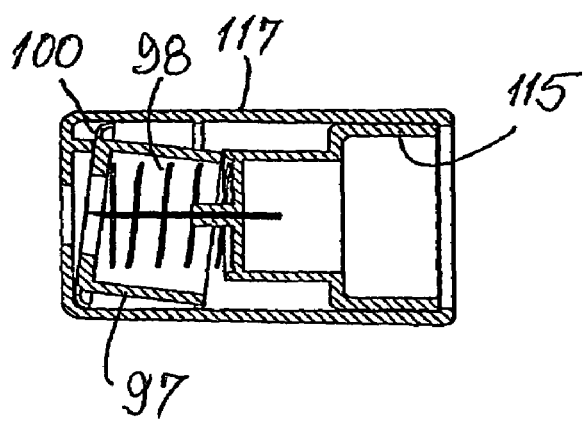
Figure 10A:
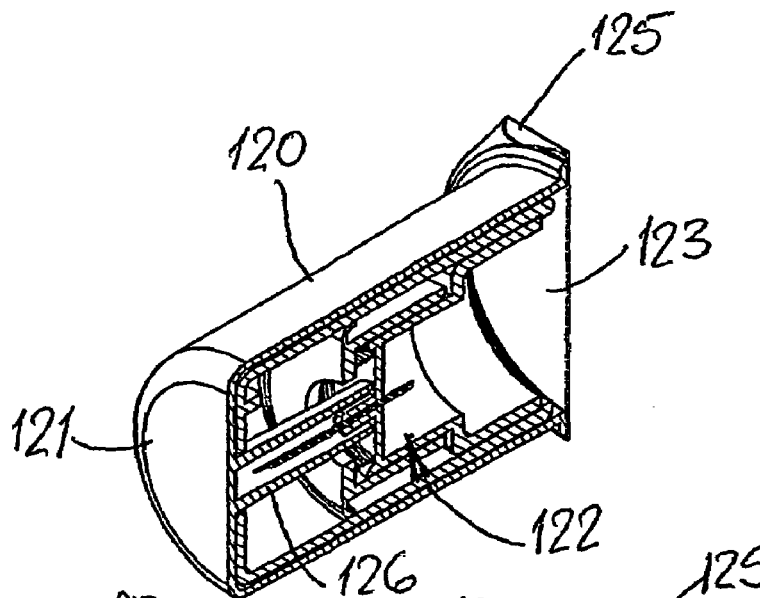
Figure 10B:
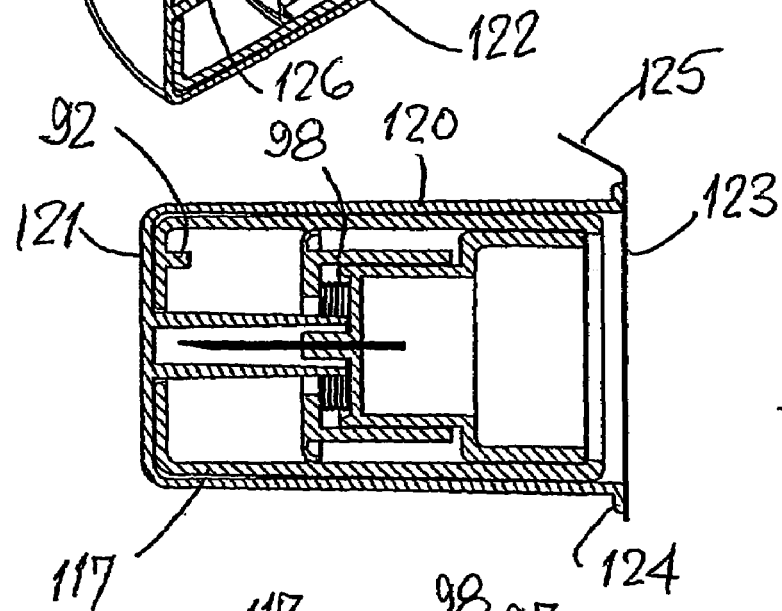
Figure 10C:
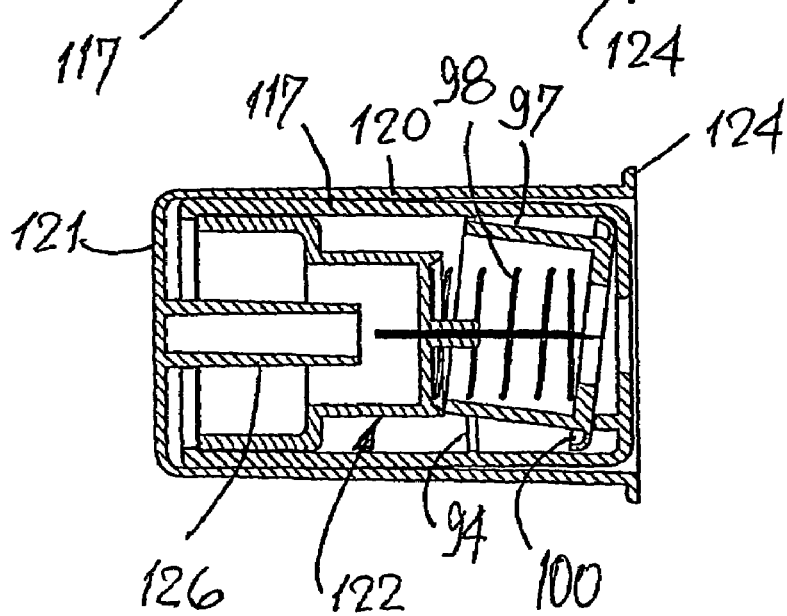
Figure 13A:
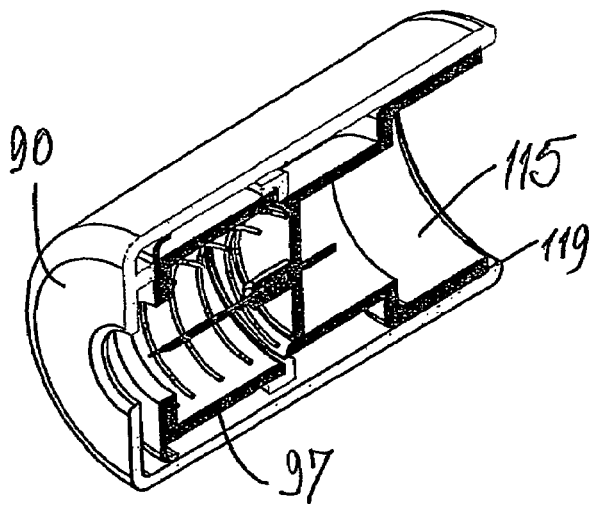
Figure 13B:
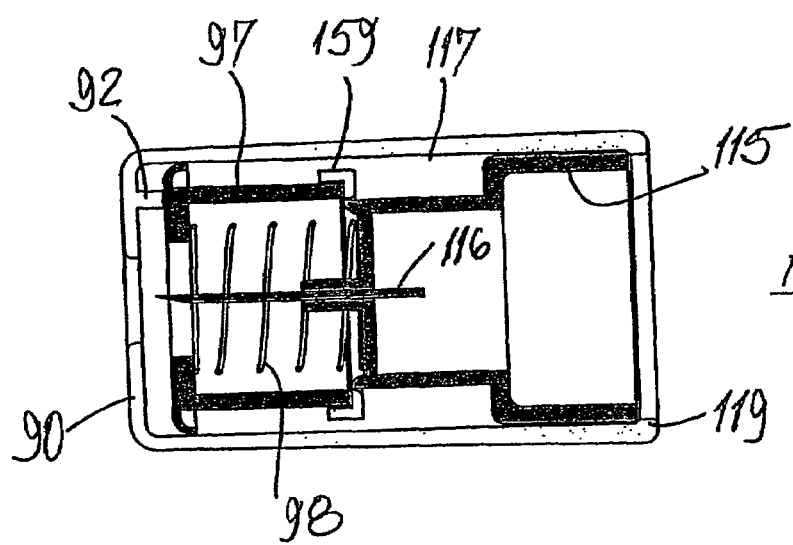
Figure 13C:
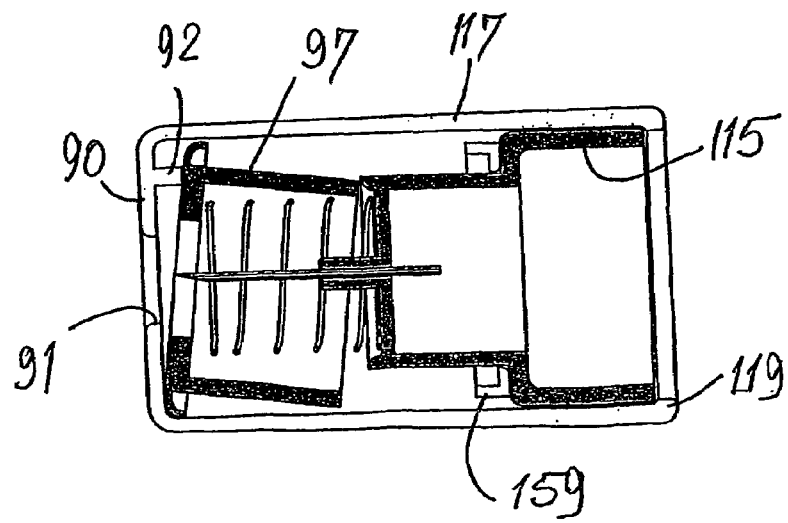

FIGS. 2A to 2E respectively correspond to FIGS. 1A to 1E, but of the second embodiment, having an external spring;

FIGS. 3A to 3D show the embodiment of FIG. 2 being used with an adapter in order to prevent the sleeve moving to its protecting position;

FIGS. 4A to 4D show the third embodiment, also having an external spring, but arranged to be resettable, with the sleeve locked in the protecting position (FIG. 4A) and then being reset, ready for reuse (FIG. 4D);

FIGS. 5A to 5E are similar to FIGS. 2A to 2E but of a fourth embodiment, having a spring external to the blocking member and being used with a syringe;

FIGS. 6A to 6E are again similar to FIGS. 2A to 2E but of a fifth embodiment not having a control member;

FIG. 6F is a view on an enlarged scale of part of the embodiment of FIG. 6A;

FIGS. 7A to 7J show a sixth embodiment of safety arrangement, intended for use with a pre-filled syringe or a syringe to be filled from a vial of medicament;

FIGS. 8A to 8J show a seventh embodiment generally similar to that of FIGS. 7A to 7J;

FIGS. 9A to 9E show an eighth embodiment intended for use with an injection device intended to take a cartridge of medicament, suitable for self-injection;

FIGS. 10A to 10C show an embodiment of packaging suitable for use with the safety arrangement of FIG. 9;

FIGS. 11A to 11M show a ninth embodiment of safety arrangement, intended for use with a single-use throw-away syringe;

FIGS. 12A and 12B show a tenth embodiment of safety arrangement similar to that but more compact than the eighth embodiment of FIG. 9; and FIGS. 13A to 13C show an eleventh embodiment of safety arrangement again for use with an injection device intended to take a cartridge of medicament.

[Note: The suffix letter I is not used in the identification of the Figures to avoid confusion with the numeral 1]

In the following description of the embodiments of this invention, the terms front, forward, and so on are used to refer to that end of the needle assembly whereat the sharp tip of the needle is located and also to the direction of insertion of the needle into a body. Conversely, the terms rear, rearwardly and so on are used to refer to the other end of the needle assembly, to which is connected other equipment such as a syringe or a blood collection system, and also to the direction of removal of a needle from a body.

Further, like components throughout the various embodiments are given like reference characters and will not be described in detail, for each embodiment.

FIGS. 1A to 1G

The first embodiment of needle assembly of this invention shown in FIGS. 1A to 1G comprises a tubular housing 10 assembled from a rear part 11 and a front part 12, permanently secured together. The rear part 11 includes a tapered socket 13 for receiving the hub of a syringe in the manner of a conventional taper-slip lock, thereby permitting the assembly to be mounted on a syringe ready for use. Internally, the rear part 11 has a boss 14 which carries the mount end of a needle 15, in a manner well known in the art.

The syringe with which the embodiment is to be used may be a pre-filled syringe, such that pre-attachment of the needle assembly immediately renders the syringe ready for use. Rather than the taper slip lock shown, a threaded connector such as a Luer lock may be employed. Alternatively, the rear part may be configured for use with known forms of phlebotomy devices for collecting blood.

Figure 1A:
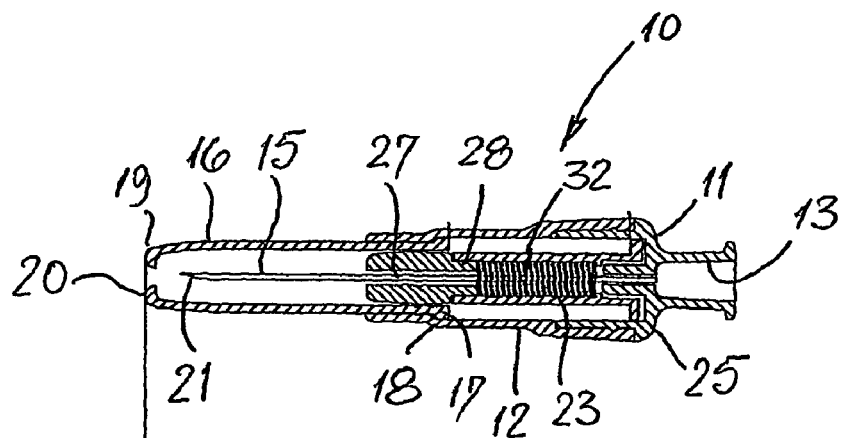
FIGS. 1A to 1E show the first embodiment, having an internal spring, with the sleeve moving from an initial position (FIG. 1A) to a fully withdrawn position (FIG. 1C) and then to a protecting position (FIG. 1E)
Figure 1B:
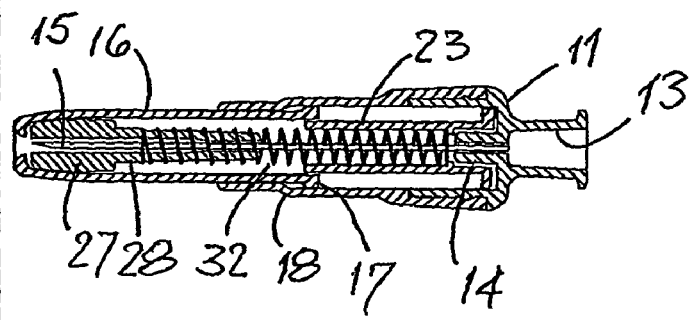
Figure 1C:
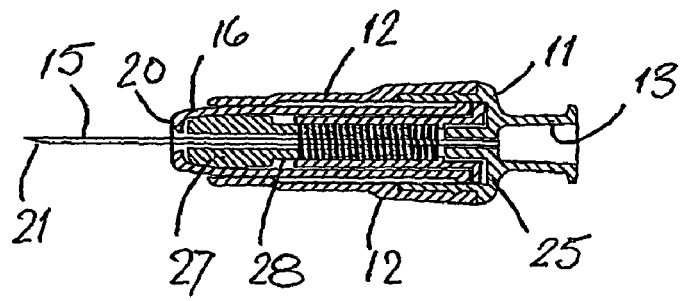

Slidably mounted in the forward region of the front part 12 is a tubular sleeve 16, the rear end of the sleeve having an external flange 17 which engages a shoulder 18 formed internally within the front part 12. The sleeve is thus constrained against further forward movement from the position shown in FIGS. 1A and 1E, but may slide rearwardly as shown in FIGS. 1B and 1C. The forward end 19 of the sleeve 16 has an in-turned lip 20 and the sleeve is of a sufficient length such that when its flange 17 engages shoulder 18, the lip 20 is disposed beyond the sharp tip 21 of the needle.

Figure 1D:
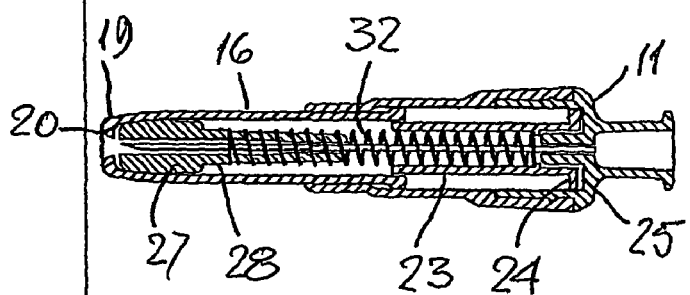
Figure 1E:
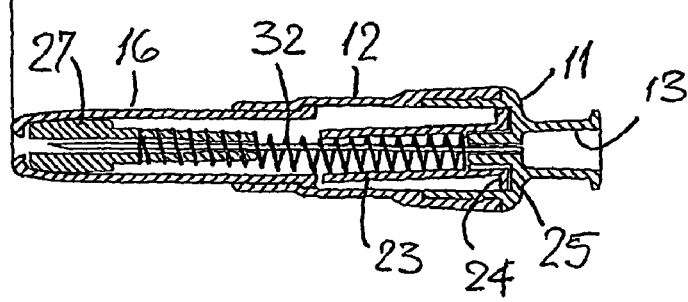
Figure 1F:
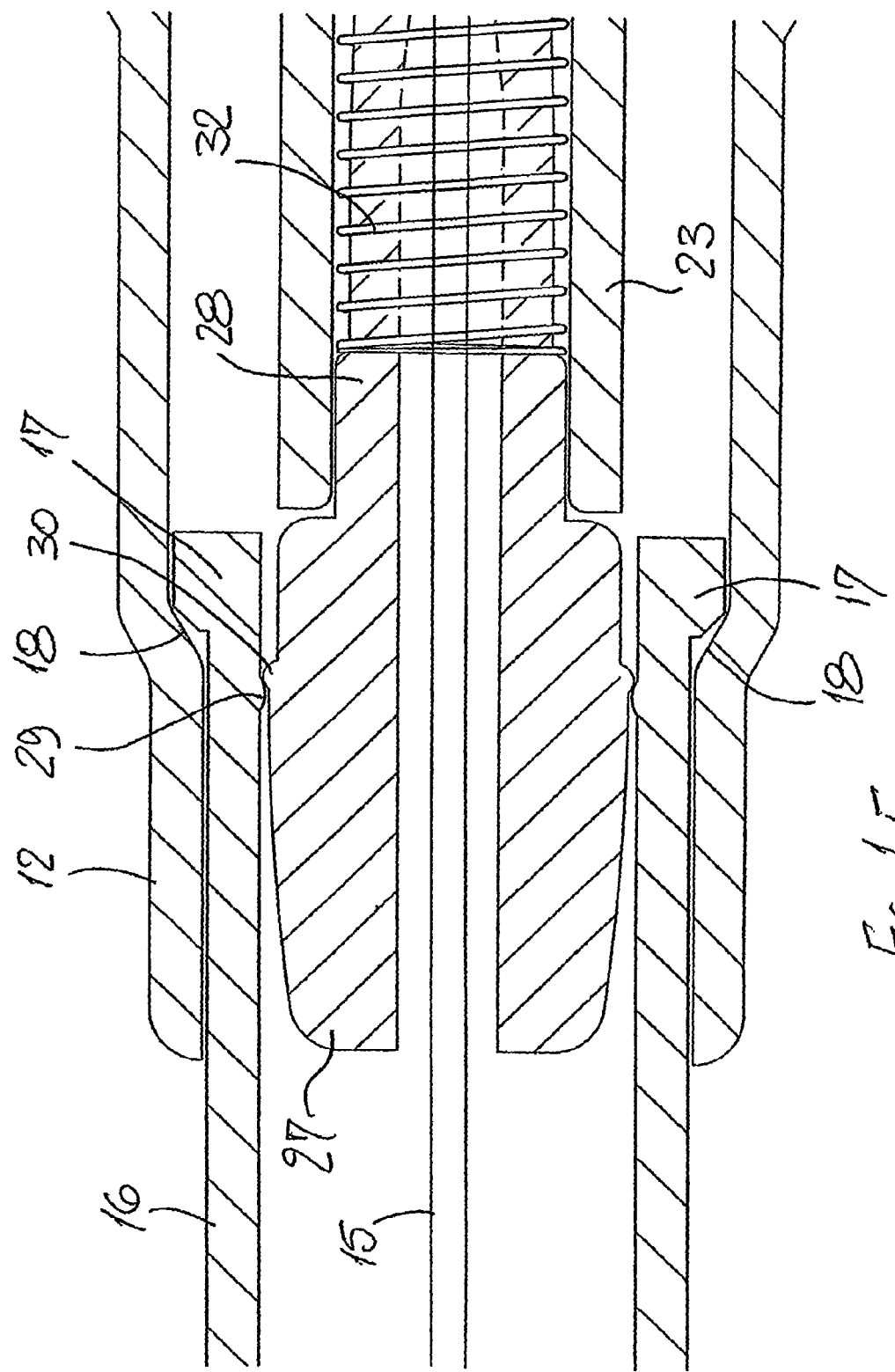
FIGS. 1F and 1G are detail views on an enlarged scale of part of the embodiment shown in FIG. 1A.
Figure 1G:
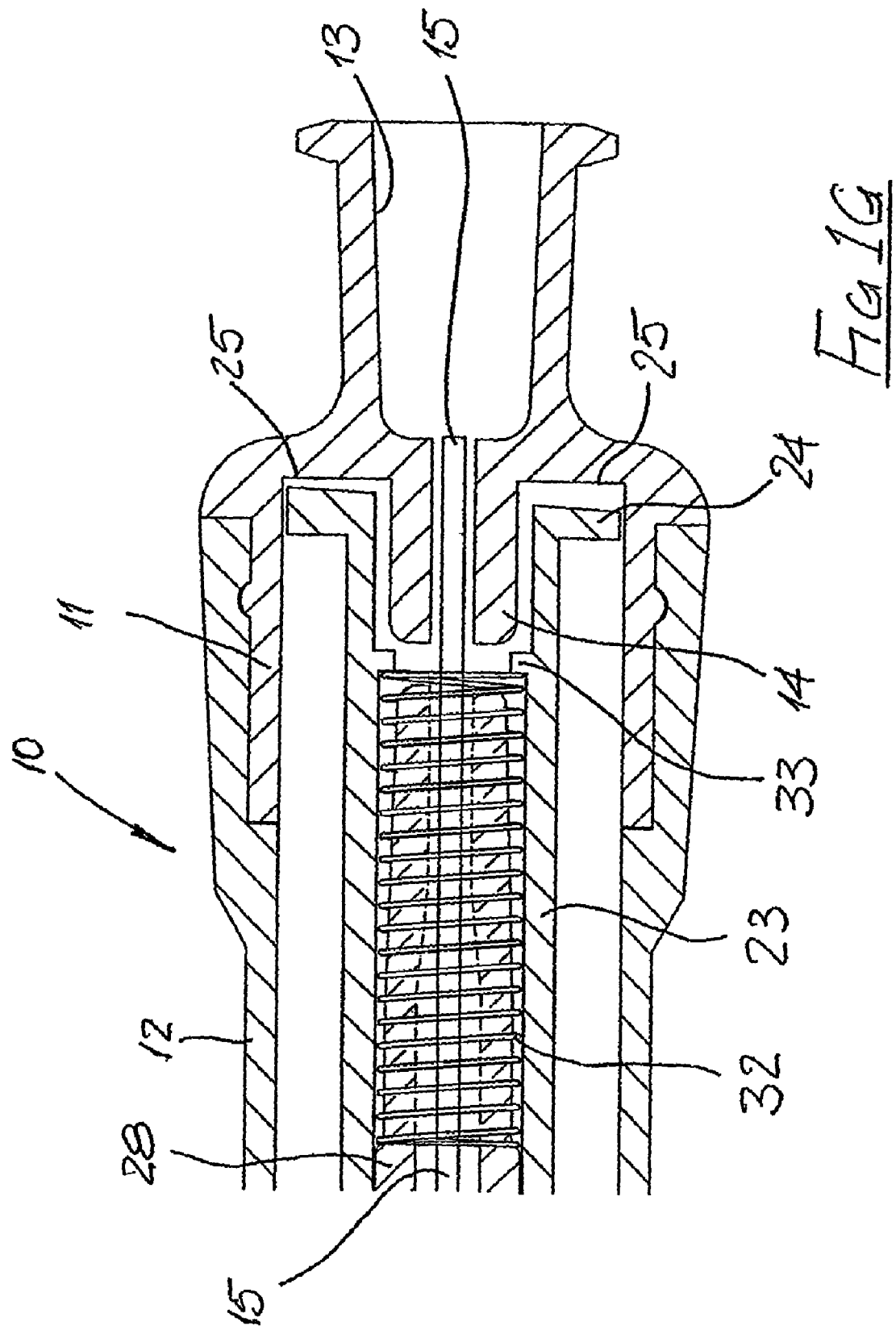

A tubular blocking member 23 surrounds the boss 14 and has a flange 24 at its rear end and disposed adjacent a radial wall 25 of the rear part 11 of the housing. The rearward facing surface of the flange 24 is non-radial with respect to the axis of the blocking member and so that face does not lie flat against the radial wall 25, as shown in FIG. 1G. The blocking member is slightly shorter than the distance between the radial wall 25 and the rear end of the sleeve, when the sleeve is fully forward, as shown in FIG. 1A.

A control member 27 is located within the sleeve 16 and has a rear portion 28 which is receivable within the forward part of the blocking member 23, the control member being profiled to limit rearward movement thereof into the blocking member. A releasable connection is formed between the control member 27 and the internal surface of the sleeve 16, shown in more detail in FIG. 1F, whereby the control member is held against movement forwardly within the sleeve 16 until sufficient force is applied to the sleeve in the rearward direction while the control member 27 is held stationary by abutting the forward end of the blocking member and the flange 24 of the blocking member 23 abuts the rear wall 25 of the housing 10. The releasable connection comprises an internal annular rib 29 engaged with an external preferably segmented annular rib 30 on the control member, or conversely the rib 29 could be segmented and the rib 30 continuous. Sufficient force on the sleeve will break the connection by causing the sleeve rib 29 to ride over the control member rib 30 whereafter the control member may slide freely within the sleeve between the internal face of lip 20 and the sleeve rib 29.

A helical compression spring 32 is disposed within the blocking member 23 and acts between the rear face of the control member 27 and an annular abutment 33 formed within the blocking member, just forward of the boss 14. The force exerted by the spring 32 is insufficient to break the connection between the control member and the sleeve when the assembly is in its initial position as shown in FIG. 1A. The rearward projection of rear portion 28 of the control member 27 is visible in FIG. 1G; this extended projection is intended to support the spring 32 to remain essentially co-axial with the needle.

The operation of the assembly described above will now be described. The initial setting is with the assembly as shown in FIGS. 1A, 1F and 1G with the sleeve 16 fully forward and wholly protecting the needle 15; the control member 27 is connected to the sleeve and is urged forwardly by the spring 32, transferring the spring force to the sleeve. In this position, flange 17 of the sleeve engages shoulder 18 of the front part 12. The rear portion 28 of the control member is located in the blocking member 23, so maintaining that member co-axial with the needle 15.

During initial rearward movement of the sleeve 16, for example by being pressed against a body, the control member is maintained stationary by the blocking member 23, in contact with the rear wall 25. If sufficient force is applied to the sleeve 16 to break the connection, the sleeve will slide on to the blocking member 23. In addition, the control member is released to move forwardly under the action of the spring, until the control member engages the internal face of the sleeve lip 20. The spring thus continues to urge the sleeve forwardly through the control member, but a force applied rearwardly to the sleeve greater than the spring force will allow continued progress of the sleeve, rearwardly.

FIG. 1C shows the sleeve in its extreme rearward position, with the needle 15 projecting to its fullest extent, from the housing 10. Here, the rear portion 28 of the control member has once more entered the blocking member and the flange 17 of the sleeve abuts the flange 24 of the blocking member. Sufficient reduction on the rearward force on the sleeve (for example, by withdrawing the assembly away from a body) will allow the sleeve to move forwards under the action of the spring, as shown in FIG. 1D. On the sleeve moving to its protecting position shown in FIG. 1E, the blocking member 23 is free of the sleeve and so moves to the position shown in that Figure, by virtue of the non-radial face of its flange 24 engaging the radial wall 25 of the housing rear part 11, under the action of spring 32. When in its non-axial position, the blocking member blocks rearward movement of the sleeve away from its protecting position, so rendering safe the needle.

It will be appreciated that in clinical use, as the sleeve 16 comes into contact with the pierceable membrane (e.g. the skin) of a body, the sleeve will automatically move rearwardly from its initial position, allowing penetration of the needle into the body. Further, once the connection between the sleeve and the control member has been broken, the mechanism will automatically lock on the return of the sleeve to the position shown in FIG. 1E. Thus, release of the sleeve from the position shown in FIG. 1B but before the sleeve has moved to the position shown in FIG. 1C will still result in the protecting position of FIG. 1E being achieved.

If the assembly is used in conjunction with a syringe to undertake drug draw-up from a phial or ampoule into the syringe, this particular assembly must be discarded and a second assembly fitted to the syringe, to perform an injection. This is in fact the preferred clinical procedure since a lubricated and uncontaminated new needle should be used for body penetration. As well as protecting the needle, the assembly has the advantage of enforcing the "new-needle" clinical procedure, even should a clinician be disinclined to follow the specified procedure.

The control member 27 is preferably made from a highly visible (e.g. strongly-coloured) plastics material, whereas the sleeve 16 is preferably made of a translucent plastics material. Thus, a simple inspection of the assembly will show whether it has been used, because the control member can be seen at the forward end of the sleeve, or whether it is ready for use, because the control member is not present within that part of the sleeve, beyond the front part 12 of the housing 10 and irrespective of the position of the control member.

FIGS. 2A to 2E

The second embodiment of FIGS. 2A to 2E is generally similar to that of FIGS. 1A to 1E, except that the connection between the control member 27 and the sleeve 16 is differently configured, and a larger spring 35 is employed, external to the blocking member 23. The spring acts between the flange 24 of the blocking member and the rear face of the sleeve 16, so directly urging the sleeve forwardly, irrespective of the sleeve position with respect to the housing 10.

A simple friction connection is employed between the control member 27 and the sleeve 16, with sufficient friction to ensure the control member remains stationary within the sleeve until sufficient force is applied to the sleeve to overcome that friction. Then, the sleeve will move rearwardly while the control member 27 is held stationary by the blocking member and so is advanced relatively, within the sleeve. Subsequently, on forward movement of the sleeve under the action of the spring 35, the control member moves forward with the sleeve and so comes free of the blocking member. Thereafter, this permits the blocking member to perform its locking action as described with reference to FIG. 1.

In this second embodiment, the amount of rearward movement of the sleeve needed subsequently to result in the disengagement of the blocking member 23 from the control member may be controlled by appropriate selection of the length of the rear portion 28 of the control member 27. With a short rear portion, only small rearward movement of the sleeve will result in an earlier disengagement of the blocking member. Conversely, with a long rear portion, a much greater rearward movement of the sleeve is required before subsequent forward movement of the sleeve disengages the control member from the blocking member.

The action with a long rear portion 28 may be advantageous where the assembly is to be used to perform drug draw-up from a phial or ampoule, before the same assembly is to be used to perform an injection, where procedures permit the same needle to be used for draw-up and subsequent injection into a body—for example with the delivery of insulin. The sleeve may appropriately be marked to show its maximum movement before locking will occur on subsequent release of the sleeve and provided that movement is not exceeded, then the assembly may be used firstly to undertake drug draw-up and secondly to perform an injection, fully inserting the needle to its correct depth, whereafter the assembly will be rendered safe.

The embodiment of FIG. 2 may be employed to give multiple injections, for example if one patient requires a plurality of intradermal injections all in the same general area. This can be achieved by using a tubular adapter 38 as shown in FIG. 3, in conjunction with the assembly of FIG. 2 (or FIG. 1) together with a syringe 39 having a syringe body 40 and a plunger 41. The needle assembly is fitted to the spigot 42 at the front of the syringe body 40 and the adapter is then slipped over the needle assembly and the syringe body (FIG. 3A). The adapter has a nose profile 43 to receive the front of the sleeve 16 and, at its other end, outwardly projecting finger grips 44.

The arrangement of FIG. 3 is used by the clinician holding the finger grips 44 together with the head 45 of the plunger 41 and moving the syringe body 40 deeper into the adapter 38, until the sleeve is fully retracted, as shown in FIG. 3D. So long as pressure is maintained between the finger grips 44 and the plunger head 45, the adapter 38 will hold the sleeve 16 in its retracted position. An increased force will be required to drive the plunger 41 into the syringe 39 to deliver a drug into the body. A reduction in that increased force should maintain the sleeve in its retracted position, so allowing the re-siting of the needle to another part of the body, for further injections. On releasing all pressure, spring 32 will move the sleeve 16 forwardly so fully protecting the needle before the syringe is removed from the adapter 38.

FIGS. 4A to 4D

This embodiment is a modified form of the second embodiment shown in FIGS. 2A to 2E. The modification is solely to the control member, which is differently profiled as shown in FIG. 4A. The control member 50 is provided with a counter-bore 51 at its forward end and the rear portion 52 tapers towards its free end. Such a control member 50 allows resetting of the assembly to a ready-to-use condition, from a locked condition.

Figure 2A:
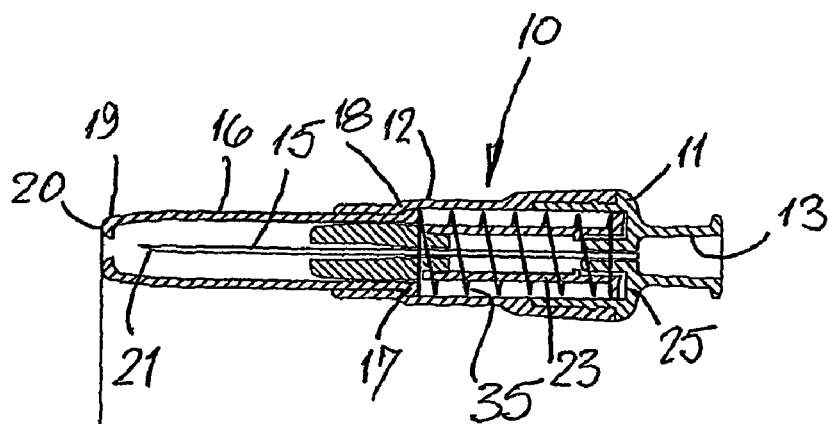
Figure 2B:
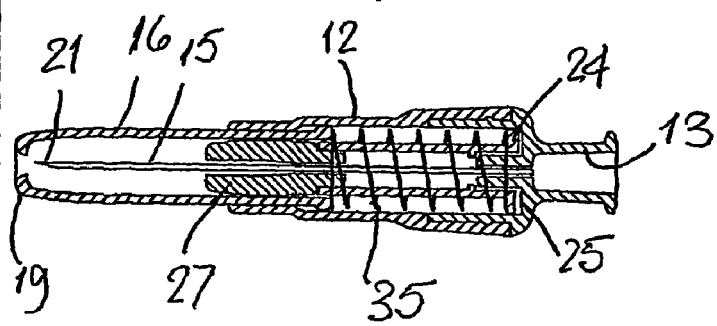
Figure 2C:
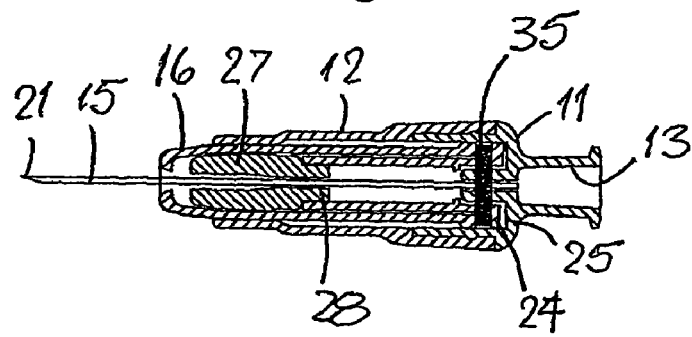
Figure 2D:
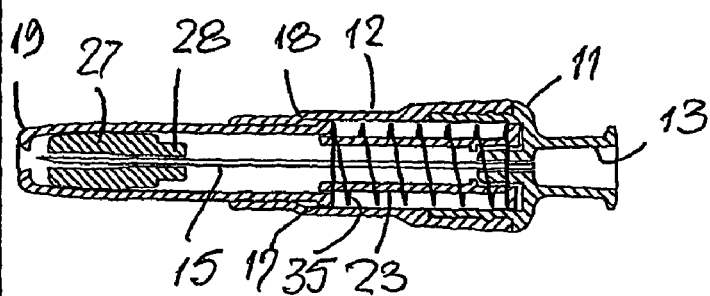
Figure 2E:
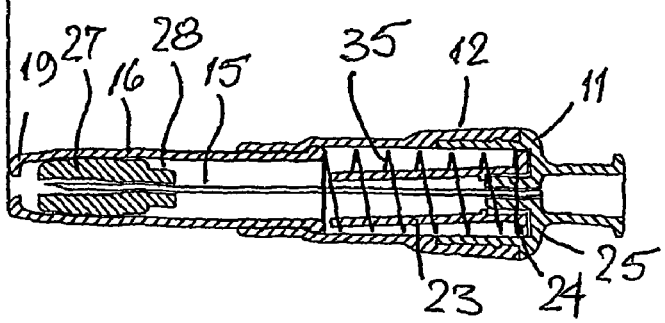

FIG. 4A shows the assembly in its protecting (locked) condition, this corresponding to the setting of FIG. 2E. The mechanism may be reset by means of a tool having a fine tubular shaft 53, receivable through the lip 20 of the sleeve 16 and into the counter-bore 51 of control member 50. Using this tool, the control member 50 may be pushed rearwardly, overcoming the friction between the control member 50 and the sleeve 16, until the control member re-enters the blocking member 23. The tapered profile of the rear portion 52 lifts the control member out of its locking position (FIG. 4B) and continued rearward movement of the control member will bring the blocking member co-axial with the needle, as shown in FIG. 4C. Removal of the shaft 53 leaves the assembly reset, ready for use.

There is no risk to a clinician in using the tool to reset the mechanism. There is no access to the needle tip until the shaft 53 has been used to complete the resetting; during insertion of the shaft, the sleeve protects the needle and no manual access can be gained to the needle tip.

FIGS. 5A to 5E

A fourth embodiment of this invention is shown in FIGS. 5A to 5E. This embodiment has a support wall 55 provided with a socket 56 to permit the assembly to be mounted on the hub 57 of a conventional syringe 58, the hub and socket together forming a conventional taper slip lock. A conventional Luer lock could be used, instead. The syringe has a cylindrical body 59 within which is mounted a plunger 60, to permit charging of the syringe and discharging of a drug, through a needle 15 supported on wall 55. A sleeve 62 has a forward portion 63 corresponding to sleeve 16 of the previous embodiments and a rearward portion 64 formed integrally with the forward portion 63. The rearward portion has a sufficient diameter to fit over the cylindrical body 59 of the syringe and is provided with an annular bead 65 at its free end, to stop the sleeve 62 coming off the wall 55.

Internally, the arrangement is essentially the same as that of the embodiment of FIG. 2, and so includes a blocking member 23, a control member 27 and a spring 35 external of the blocking member. The control member 27 is a frictional fit within the forward portion 63 of the sleeve 62 and so may be slid forwardly within the forward portion, as the sleeve 62 is moved rearwardly. As previously, sufficient forward movement of the control member within the forward portion 63 allows the blocking member 23 to move to its inclined position shown in FIG. 5E once the sleeve 62 has moved to its protecting position, so thereafter preventing retracting movement of the sleeve.

FIGS. 6 to 13

The embodiments of FIGS. 1 to 5 all employ a separate and movable control member such as member 27 of FIG. 1, whereas the embodiments of FIGS. 6 to 13 have no such control member. Rather, control of movement of the blocking member is achieved by alternative means, as will be described.

FIGS. 6A to 6F

The fifth embodiment is shown in FIGS. 6A to 6F. This does not include a control member, but otherwise is similar to the second embodiment, shown in FIGS. 2A to 2E. In this fifth embodiment, at least one stop 70 is formed internally within the rear part 11 of the housing 10, adjacent but spaced from the inner face of the radial wall 25. In addition, the sleeve 71, though generally similar to sleeve 16, has a shoulder 72 part way therealong, for engaging the blocking member 23 once the sleeve has been moved sufficiently, rearwardly.

The or each such stop 70 is appropriately configured to hold the blocking member 23 away from the radial wall 25. The blocking member 23 has such a length that when it bears on the stops 70 and the sleeve 71 is in its initial position, the blocking member is located within the rear end of the sleeve 71, as shown in FIG. 5A. In this position, the force exerted by the spring 35 is insufficient to move the flange 24 of the blocking member over the or each stop 70.

On moving the sleeve rearwardly, the shoulder 72 of the sleeve will abut the forward end of the blocking member 23. Thereafter, sufficient pressure on the sleeve will press the flange 24 of the blocking member 23 over the stops 70, to engage the radial wall 25 of the housing rear part 11.

From this point, operation is as with the second embodiment of FIG. 2. Movement of the assembly away from a body allows the sleeve 71 to move forwardly under the action of the spring 35, and when fully forward, the blocking member 23 is inclined to the needle axis by virtue of the inter-engagement of the non-radial flange 24 of the blocking member with the radial face of wall 25. The blocking member thus blocks subsequent movement of the sleeve 71, towards its retracted position.

FIGS. 7A to 7J

The sixth embodiment is shown in FIGS. 7A to 7J. The safety arrangement is intended for use with a syringe having a body 80 fitted with a needle 81 in the course of manufacture. The syringe has a plunger 82 with a piston 83 within the bore of the syringe, so that liquid may be drawn into the syringe through the needle 81 by withdrawing the plunger 82 from its fully inserted position, the medicament subsequently being expelled through the needle 81 by depressing that plunger.

The plunger 82 has an X-shaped cross-section and differs from the plunger of a conventional syringe in that the outer edge of each arm of the X-shaped cross-section is provided with a protuberance 84, disposed approximately one quarter of the way along the length of the plunger, from the piston end. In the region of each protuberance, the respective arm has a through-slot 85 to enable radially inward movement of the protuberances. The protuberances 84 define a stop position for the plunger on being moved into the bore by the application of axial pressure to the remote end 86 of the plunger. When the protuberances reach the rear end of the syringe body, an increased force is momentarily required to move the plunger deeper into the syringe body.

Figure 7A:
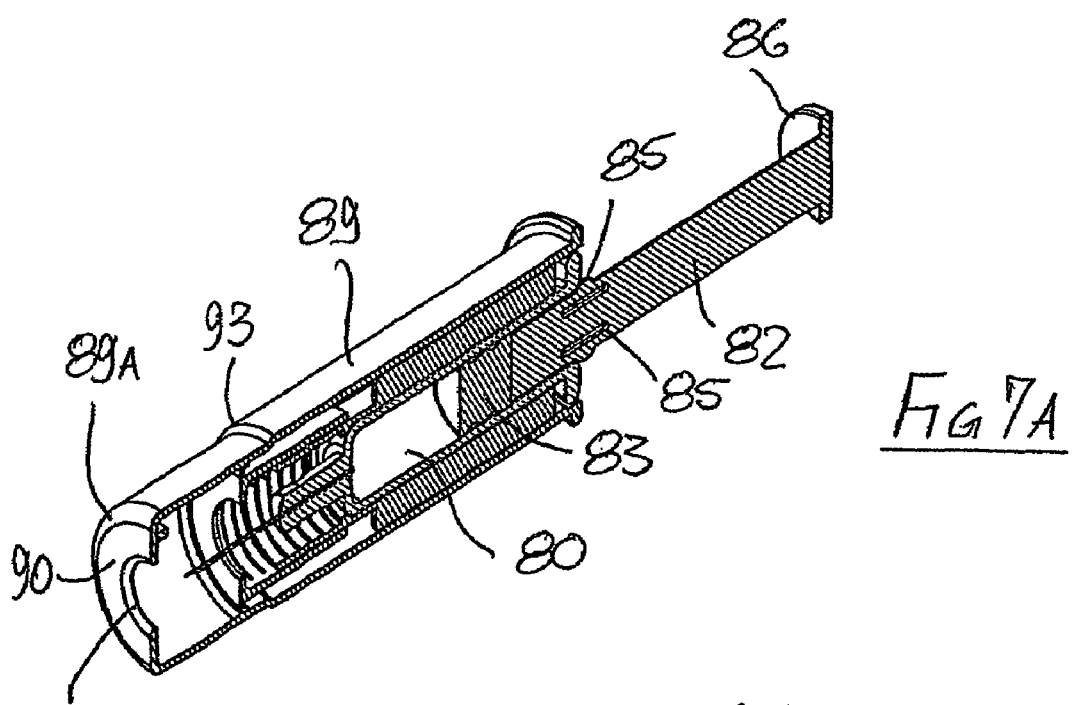
Figure 7B:
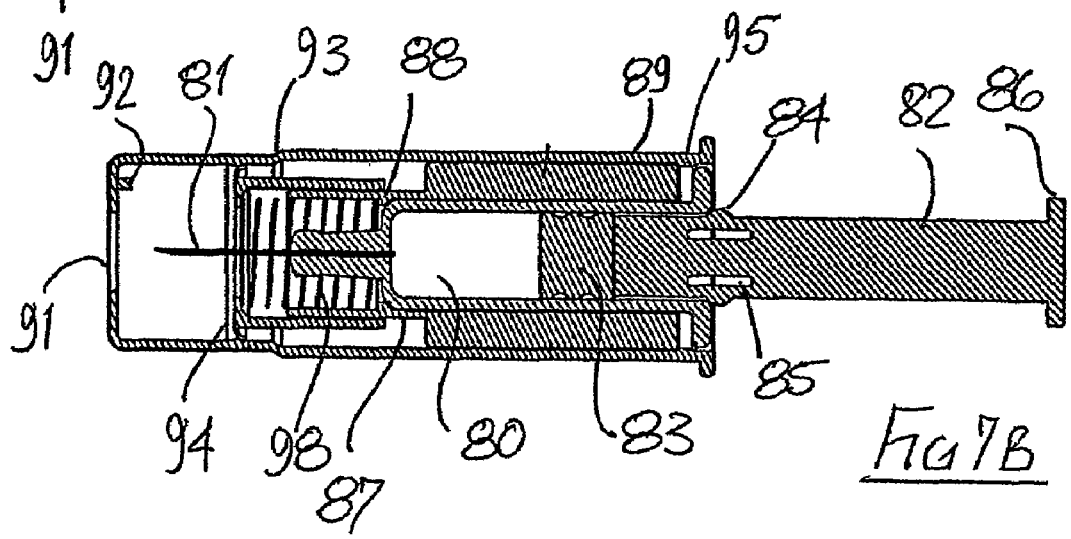
Figure 7C:
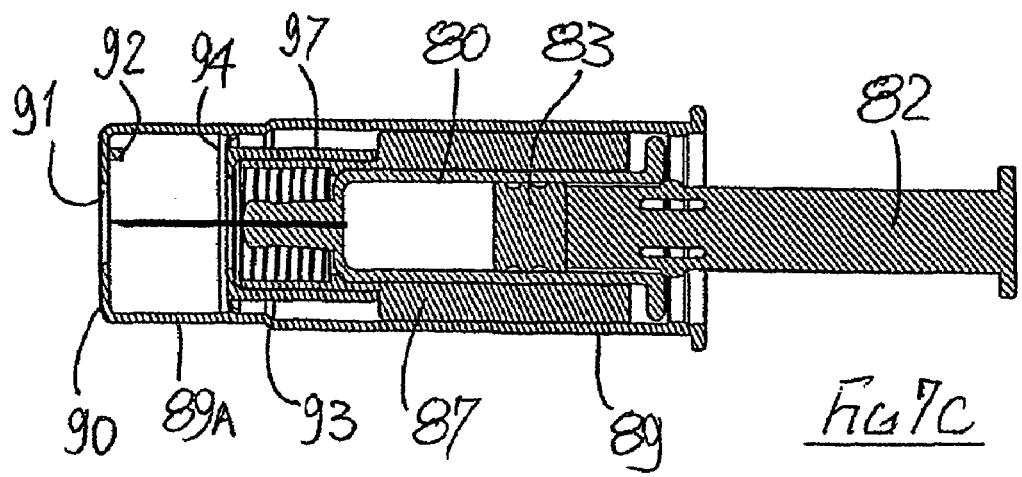
Figure 7D:
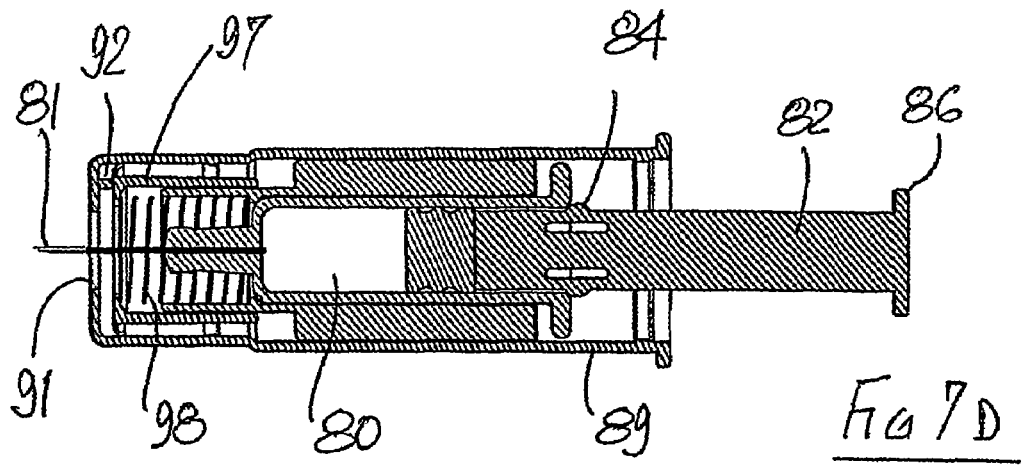
Figure 7E:
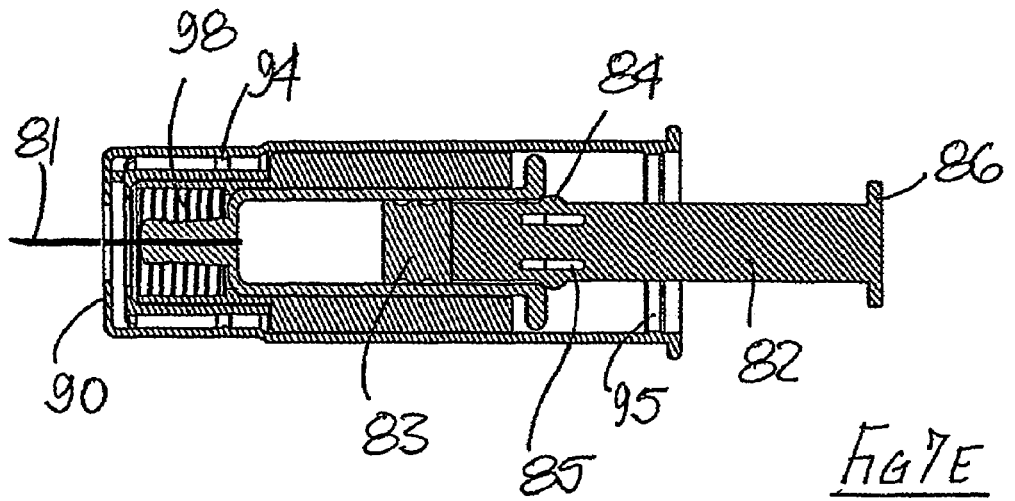

The safety arrangement for use with the syringe described above comprises a tubular support 87 having a bore in which the syringe body 80 is snugly received. The needle is thus indirectly carried by the support, through the syringe itself. Formed within that bore is an internal rib 88 which limits the movement of the syringe body into the bore. The part of the support 87 which overlies the syringe body has a greater wall thickness and slidably carries a sleeve 89. The forward end 89A of the sleeve has an internal radial flange 90 formed with a central hole 91 through which the needle 81 may project, the flange being provided with an upstand 92 which projects internally of the sleeve towards the syringe, the upstand having a relatively small arcuate extent, typically of only a few degrees. Partway along the length of the sleeve 89, an annular shoulder 83 is formed by a change in the internal and external diameters of the sleeve and between that shoulder 93 and the flange 90, there is formed an inwardly-projecting annular rib 94 (FIG. 7J). A further internal rib 95 (FIG. 7H) is formed at the rearward end of the sleeve, over which an out-turned flange 96 at the rear end of the syringe body must ride to permit the sleeve to slide rearwardly from that position shown in FIGS. 7A, 7B and 7J.

A tubular blocking member 97 is slidably carried on the forward end portion of the support 87 and is urged forwardly by a helical compression spring 98, acting between the internal rib 88 of the support and an internal flange 99 formed at the forward end of the blocking member 97. Externally, the blocking member 97 has at its forward end an outwardly-projecting flexible lip 100 slidable within the smaller diameter portion of the sleeve 89 but movable over the internal rib 94 of the sleeve only when an increased force is applied to the sleeve, relative to the blocking member. This is shown on an enlarged scale in FIG. 7K.

The starting position is shown in FIGS. 7A, 7B, 7J and 7K, with the safety arrangement set ready for use, though the plunger will be fully forward, to permit filling of the syringe. Alternatively, the syringe could be pre-filled, in which case the plunger will be set as shown, and the filling step will be omitted.

If the syringe is to be filled, the nose part of a phial (not shown) of medicament is inserted into the hole 91 at the forward end of the sleeve 89 and is pushed gently on to the needle 81, moving the sleeve rearwardly with respect to the syringe by riding the further rib 95 of the sleeve over the out-turned flange 96 of the syringe body 80. During this, the blocking member 97 moves rearwardly, simultaneously with the sleeve, against the action of spring 96. The combined force of the spring 96 acting on the blocking member 95 and the force required to ride the further rib 95 over the out-turned flange 96 should be less than that required to move the lip 100 of the blocking member 97 over the rib 94 of the sleeve. As such, during the phial-filling operation, the blocking member 97 remains with its lip 100 rearward of rib 94 of the sleeve (FIG. 7C).

Following charging of the syringe and then the removal of the phial, the mechanism is ready for performing an injection. The operator applies a gentle force on the remote end 86 of the plunger by applying a reaction to the sleeve 89 and this has the effect of moving the plunger forwardly until the protuberances 84 are about to enter the syringe body, and also of pulling the sleeve rearwardly, to cause the needle 81 to project from the forward end of the sleeve. However, this can be achieved only by having the lip 100 of the blocking member 97 ride over the rib 94 of the sleeve 89 and so moving forwardly towards the flange 90 of the sleeve, as shown in FIG. 7D. Rearward movement of the sleeve may continue until the shoulder 93 engages that part of the support having a thickened wall thickness as shown in FIG. 7E. The needle 81 is then projecting beyond the flange 90 to its greatest possible extent.

Figure 7F:
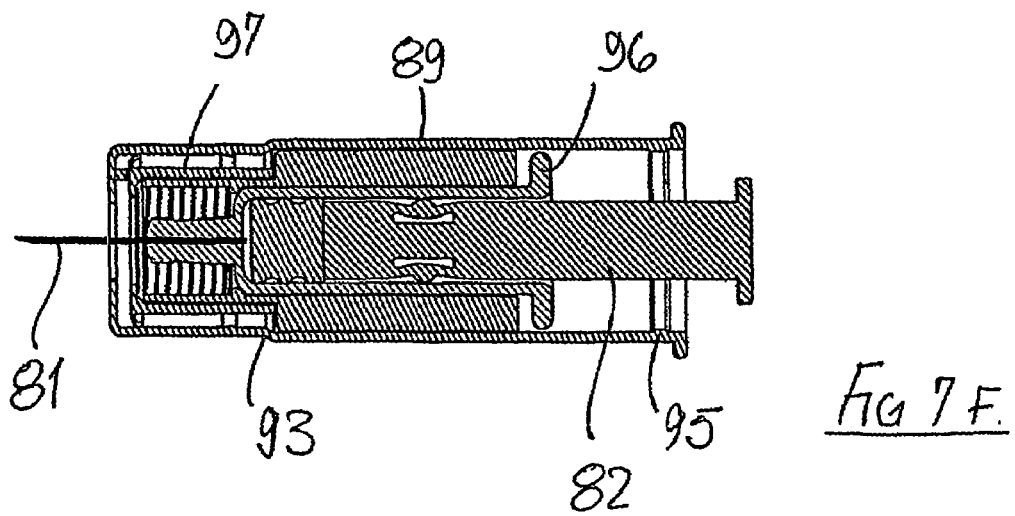

The assembly is used in this condition to perform an injection, firstly by pushing the needle 81 into a body at the injection site and then pushing the plunger fully forwardly, the protuberances 84 moving inwardly to permit this, as shown in FIG. 7F. The condition of FIG. 7E could instead be achieved by using the syringe with the connected assembly to perform a stabbing motion against a body, so that the engagement of the flange 90 at the forward end of the sleeve moves the sleeve rearwardly with respect to the syringe.

On removing the syringe assembly from a body, by pulling rearwardly on the plunger and releasing the sleeve, or by pulling on the sleeve and releasing the plunger, the spring 98 will cause relative separation of the forward end of the sleeve and the support 87, the spring acting on the flange 99 of the blocking member 97 to maintain contact between the forward end of the blocking member and upstand 92. Eventually, the separation will be so great that the blocking member comes free of the support 87 and the spring force acting on the blocking member will allow it to cant over so that its axis lies at an acute angle to the axis of the sleeve and support member—FIG. 7G. When in this position, the blocking member 97 lies between the flange 90 of the sleeve and the forward end of the support 87 and so physically blocks subsequent rearward movement of the sleeve 89, with respect to the support and syringe.

Figure 7G:
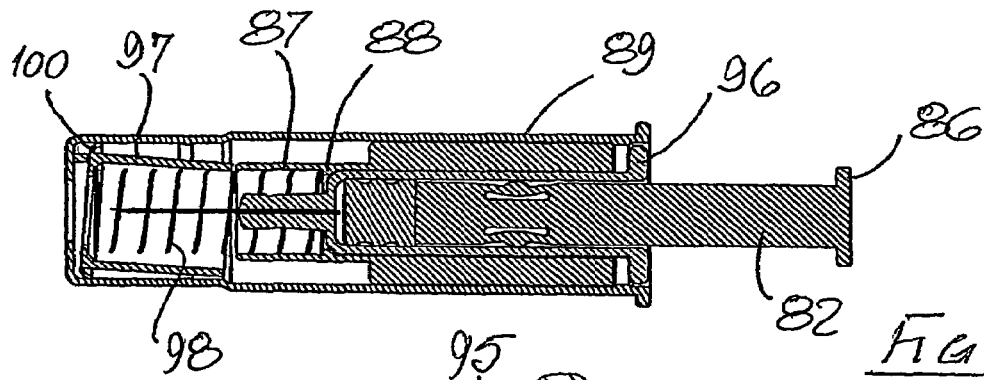
Figure 7H:
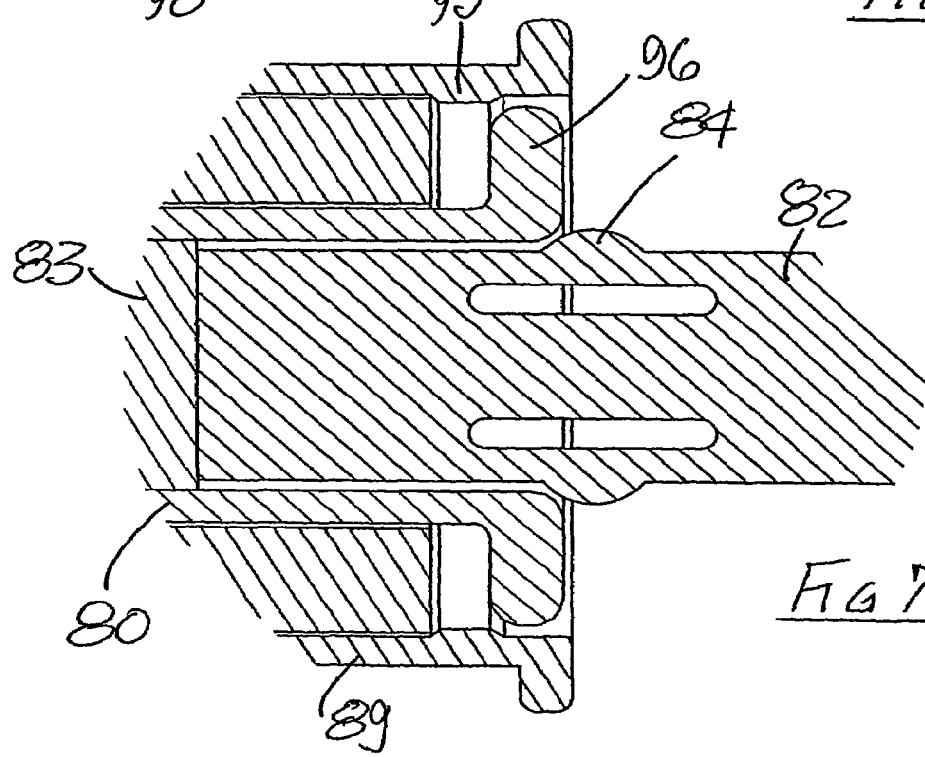
Figure 7J:
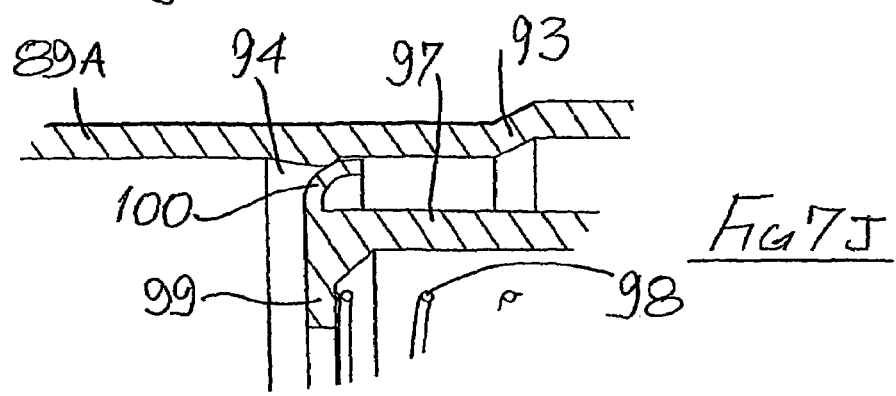

When in the setting of FIG. 7G, the needle is securely protected against exposure. Having regard to the tubular nature of the blocking member 97, a very high force must be applied to the sleeve 89 in order to expose the needle, in effect either destroying the sleeve or the blocking member.

FIGS. 8A to 8H

The seventh embodiment is shown in FIGS. 8A to 8H. This seventh embodiment is generally similar to the sixth embodiment of FIGS. 7A to 7J and like parts are given like reference numbers and will not be described again in detail.

The seventh embodiment differs from the sixth embodiment in that the part of the support 104 surrounding the syringe 80 does not have a significantly increased wall thickness, though a step 105 is formed between forward and rearward parts of that support, in order to serve as a backstop for movement of the blocking member 97. At its rearward end, the support 104 has an increased internal diameter portion 106, to permit the accommodation therein of the out-turned flange 96 of a syringe, which may have an entirely conventional plunger not including the protuberances 84 of the sixth embodiment. That increased diameter part 106 supports a tube 107 projecting forwardly coaxial with the support itself but with an annular space between the tube and the support. A sleeve 108 is slidably mounted within the tube 107, forward movement of the sleeve being limited by an external rib 109 around the rear end of the sleeve and an internal shoulder 110 formed within the tube 107.

The sleeve has two axially-spaced internal ribs 111 and 1 12, each of which can interact with the lip 100 of the blocking member 98 in a generally similar manner to that described with respect to the sixth embodiment.

Figure 8A:
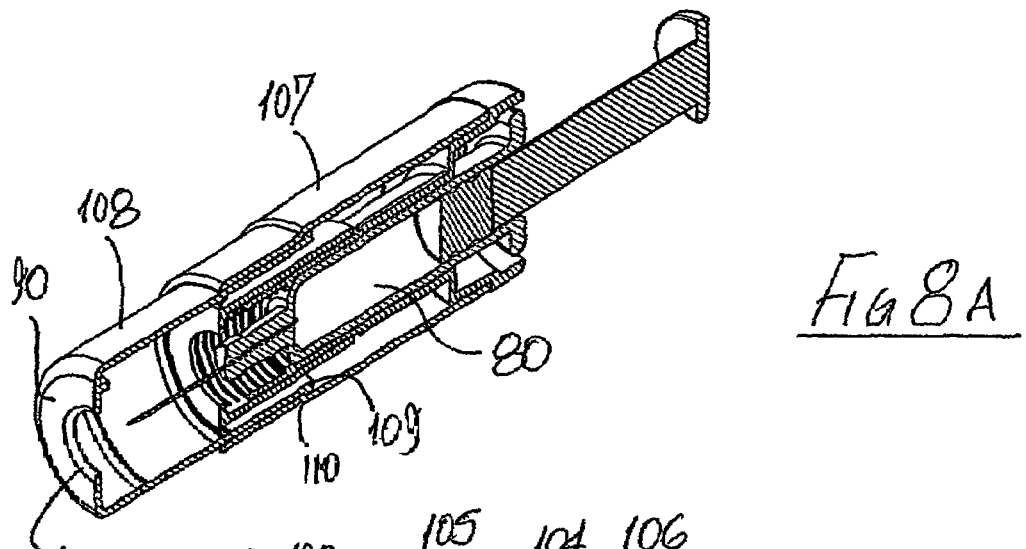
Figure 8B:
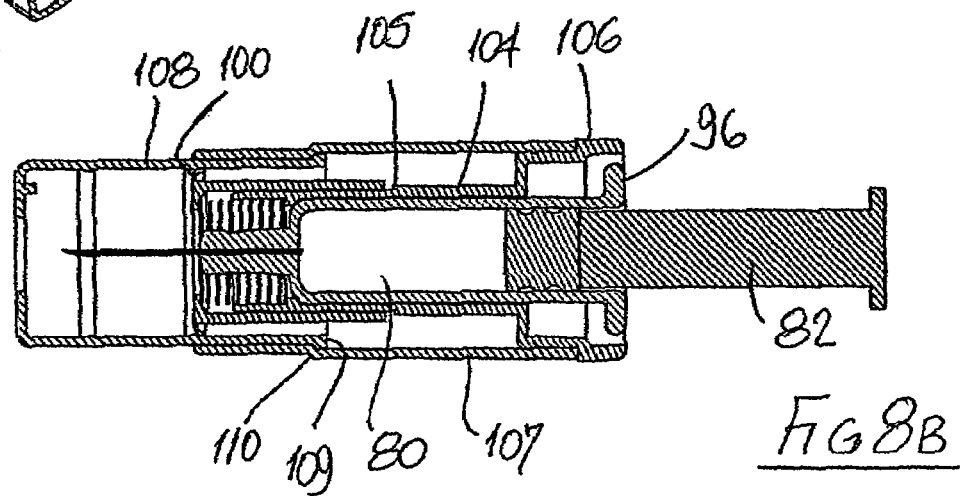
Figure 8C:
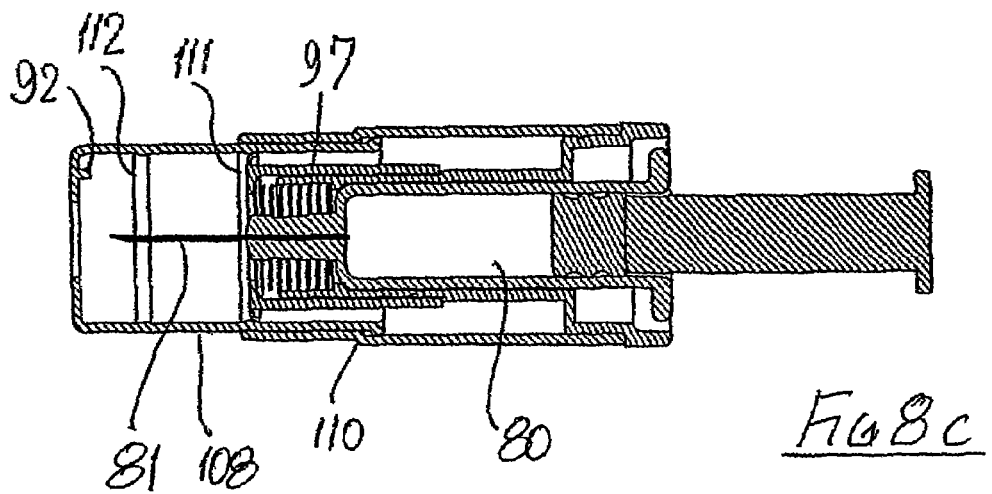
Figure 8D:
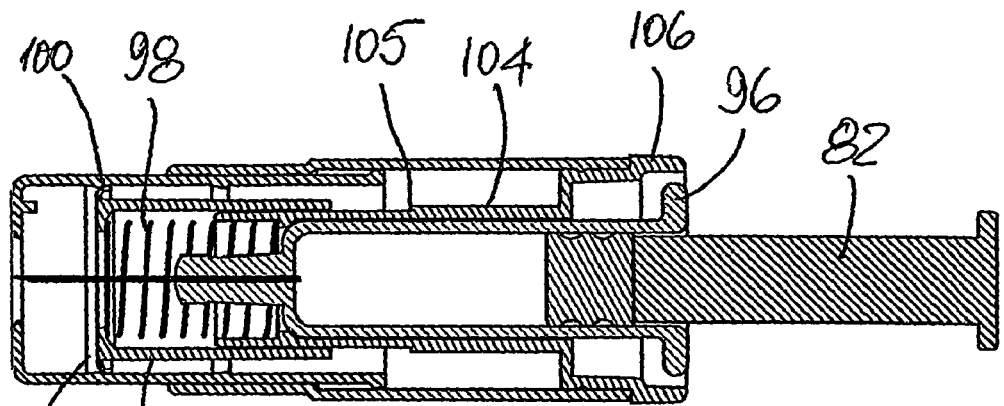
Figure 8E:
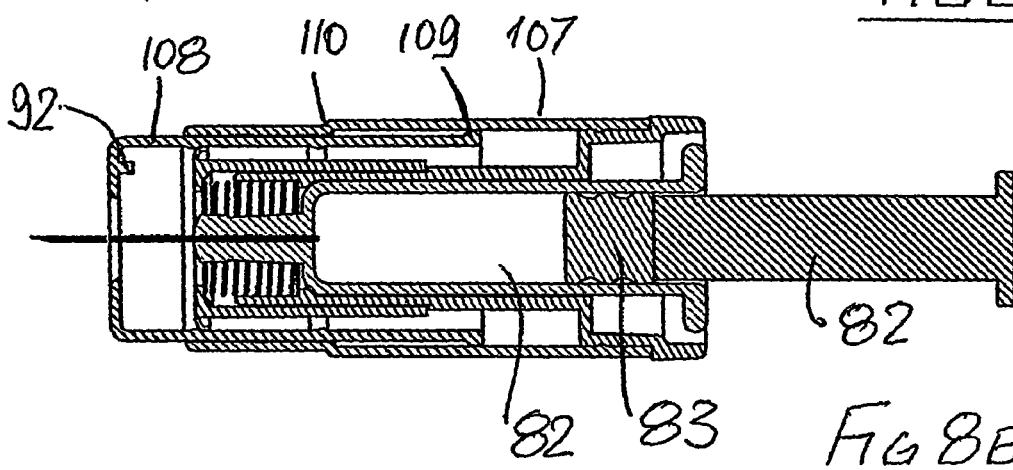
Figure 8F:
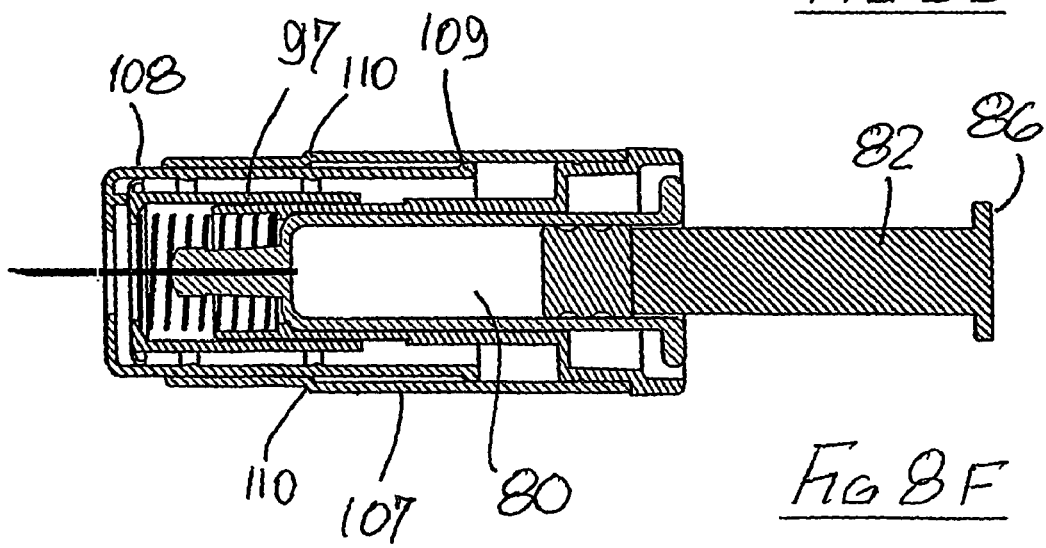
Figure 8G:
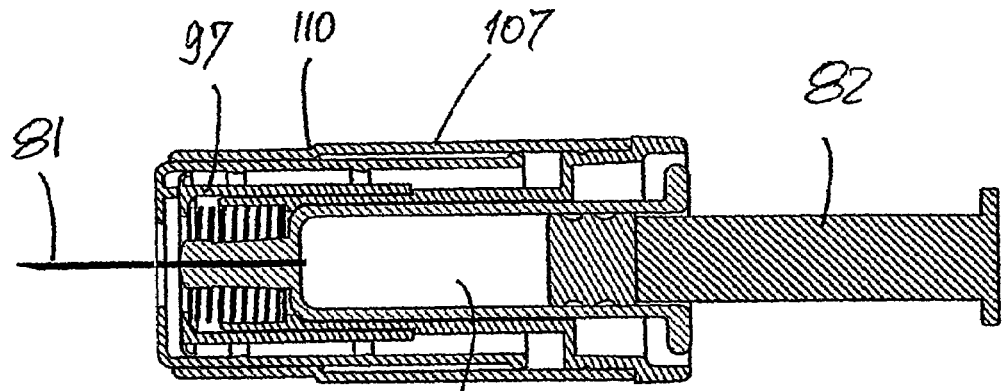

FIGS. 8A and 8B show the initial position, with a slight clearance between the rearward end of the blocking member 97 and the step 105 of the support 104. On loading a phial for the filling of the syringe, initially the sleeve moves rearwardly until the rear end face of the blocking member engages the step 105 (FIG. 8C) and continued rearward pressure on the sleeve then allows the lip 100 of the blocking member to ride over the first rib 111, then to move forwardly to engage the second rib 112 (FIG. 8D). In this setting, the syringe may be filled from a phial and on releasing the phial from the syringe, the sleeve and blocking member will together move forwardly to the position shown in FIG. 8E, so covering the needle once more.

Figure 8H:
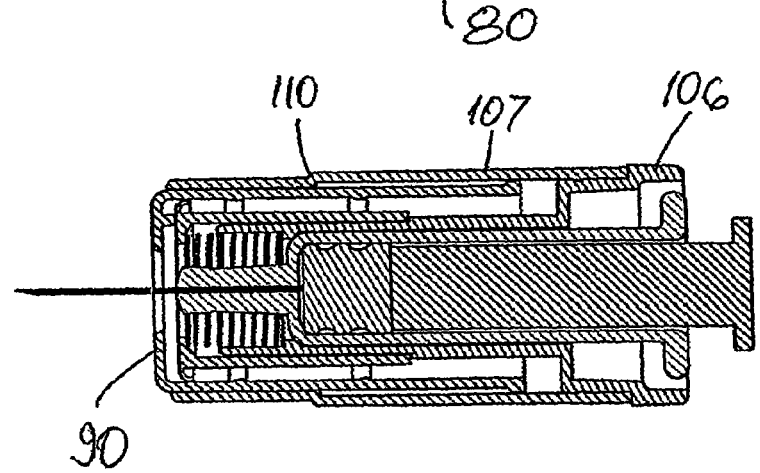
Figure 8J:
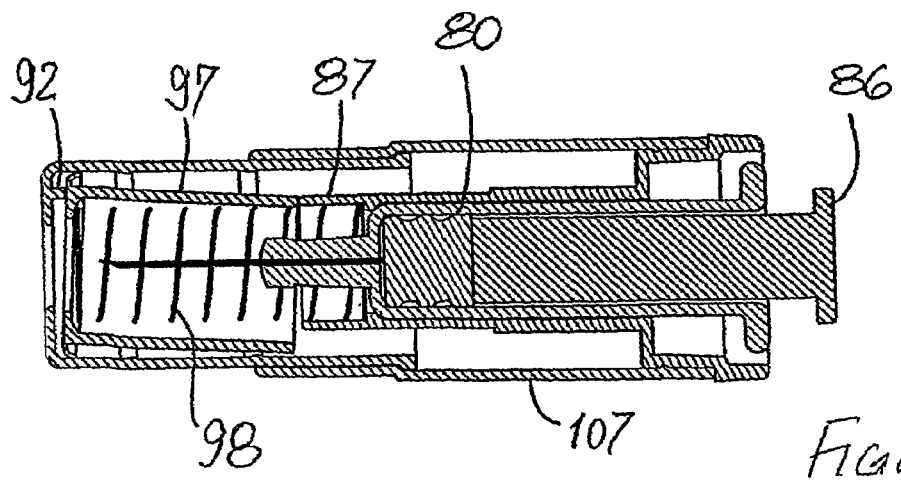

From this setting, operation is essentially as described in relation to the sixth embodiment. Thus, the syringe assembly is used to make an injection in the course of which the blocking member 97 moves fully forwardly (FIG. 8F) and then further rearward movement of the sleeve allows the needle to project to its greatest possible extent (FIG. 8G), as the plunger is depressed (FIG. 8H). On withdrawing the needle, the sleeve 108 is moved forwardly under the action of the spring bearing on the blocking member; finally the blocking member 97 comes free of the support 104 and is canted over (FIG. 8J) so as to provide a physical block between the support and the flange of the sleeve, as described above.

FIGS. 9A to 9E

The eighth embodiment is shown in FIGS. 9A to 9E and is a modified form of the sixth embodiment (FIGS. 7A to 7J) intended for use with an injection device adapted to receive a cartridge of medicament. For example, the safety assembly of this eighth embodiment may be employed with a medicament-dispensing "pen" intended for dispensing a pre-selected but variable dose of insulin, for self-injection.

A support 115 directly carries a needle 116 the rear end of which projects into the space within the support 115, so that on fitting the support to an injection device carrying a cartridge of medicament, the rear end of the needle will penetrate a membrane at the forward end of the cartridge. The needle 116 so thus communicates with the interior of the cartridge, for dispensing of the medicament.

A sleeve 117 is slidably mounted on the rearward part 118 of the support 115 and has an in-turned lip 119 to prevent the sleeve moving forwardly with respect to the support, from the position shown in FIGS. 9A and 9B. The forward end of the sleeve, its rib 94 and the blocking member 97 are all as described with respect to the sixth embodiment and are given like reference characters; these components will not be described further here.

In the initial position shown in FIGS. 9A and 9B, the spring 98 is shown fully compressed but the force exerted thereby on the blocking member 97 is insufficient to move the lip 100 of the blocking member over the rib 94 of the sleeve. Equally, as discussed above, the support 115 cannot move out of the sleeve by virtue of the in-turned lip 119 at the rear end of the sleeve.

When an injection (and typically a self-injection of insulin) is to be made, the safety arrangement is mounted on the front end of an injection pen, the appropriate dose is set and then the pen is used to perform a stabbing motion on the selected body site. The flange 90 at the forward end of the sleeve 117 serves to ensure that the needle 116 enters the body essentially perpendicularly and the impact force on the body of the flange 90 at the forward end of the sleeve 117 serves to cause rib 94 to ride over lip 100 of the blocking member. This allows the blocking member 97 to move forwardly under the action of spring 98, as shown in FIG. 9C. From there, the operation is essentially as described above with reference to the sixth embodiment of FIG. 7. The injection is performed with the assembly set as shown in FIG. 9D and, following withdrawal of the needle, the sleeve is blocked in its protecting position as shown in FIG. 9E.

FIGS. 10A to 10C

Packaging for the eighth embodiment of FIG. 9, is illustrated in FIGS. 10A to 10C. The safety device itself shown in these Figures is identical to that of FIGS. 9A to 9E and will not be described again. Further, the same reference numbers are used to designate the same components.

The packaging comprises a moulded plastics cylindrical tube 120 closed at one end by wall 121, and shaped to receive the safety assembly 122 of FIGS. 9A and 9B in its initial condition as shown in FIGS. 10A and 10B. When so received, the tube 120 containing the assembly 122 may be rendered sterile, using known techniques, and then sealed by a cover foil 123 heat-sealed to a flange 124 around the open end of the tube 120. That foil has a flap 125 to enable easy opening of the tube, when the assembly 122 is to be used.

As shown in the drawings, a cylindrical projection 126 upstands axially from the end wall 121 of the tube 120. That projection has such a length that when the assembly 122 is fully received in the tube 120, the inner end of the projection engages the blocking member 97 of the assembly and so prevents that blocking member moving forwardly under the action of spring 98, notwithstanding the interengagement of the lip 100 with rib 94 of the sleeve 117.

Figure 11C:
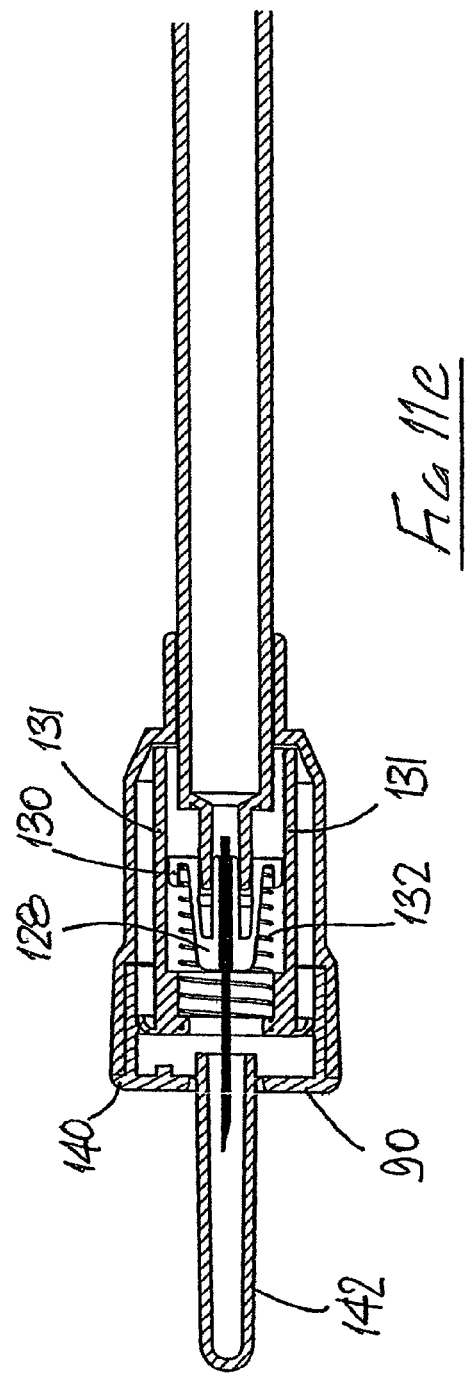
Figure 11D:
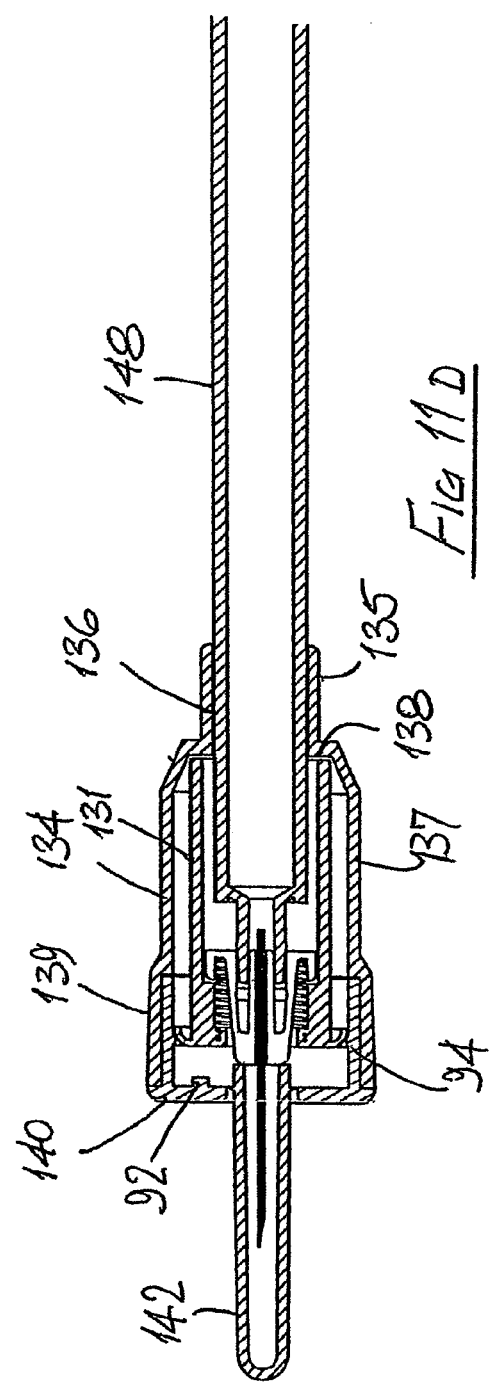

After opening the tube, the injection pen is pressed on to the assembly 122 while still in the tube 120 and then the tube is pulled free of the assembly. Following use of the safety assembly to make an injection, the sleeve protects the needle as the blocking member prevents the sleeve being withdrawn to expose the needle, as shown in FIG. 11C. The assembly may then be inserted into the tube 120 but the other way round (that is, with the needle pointing towards the open end of the tube) and, having regard to the draw of the tube, as the assembly is pushed fully home it forms a tight frictional fit within the tube. As such, it will be extremely difficult to withdraw the assembly once more and the needle is fully protected, for disposal.

FIGS. 11A to 11M

The ninth embodiment is shown in FIGS. 11A to 11M. This safety arrangement is intended for use with a single-use luer-slip or luer-lock syringe having a syringe body 148 moulded from a plastics material and provided with a luer-lock taper spigot 149 at its forward end, for receiving a correspondingly profiled needle hub. Such syringes are well known in the art and are very widely used; following use of the syringe, it is thrown away with the needle still connected to the syringe.

The safety arrangement of this ninth embodiment has a support 128 provided with a needle 129, the support defining a socket to receive the luer-lock spigot 149 at the forward end of the syringe 148. The support 128 defines an outer cylindrical surface 130 on which a blocking member 131 is slidably carried, a spring 132 acting between the support 128 and the forward end of the blocking member 131. A two-part sleeve 134 surrounds the support 128 and the blocking member 131, the rearward end portion 135 of the sleeve defining a cylindrical bore 136 within which the outer surface of the syringe body 148 is slidably receivable. The transition between that rearward end portion 135 and the central region 137 of the sleeve forms a shoulder 138 against which both the support 128 and the blocking member 131 abut, with the assembly in its initial position as shown in FIGS. 11A and 11B.

The forward end portion 139 of the sleeve 134 has an enlarged diameter and carries a front sleeve part 140 configured similarly to the front part of the sleeve of the sixth and eighth embodiments. Thus, this front part 140 has a flange 90 at its forward end together with an upstand 92 on that flange, and an annular rib 94 is formed internally, spaced rearwardly from the flange 90. Further, the forward end of the blocking member 131 has a lip 100 to co-act with the rib 94, again as described above.

A protective tubular cap 142 is moulded integrally with the front part 140 but is connected to the front part by relatively weak ribs around the hole 91 in the flange 90. The cap projects internally into the sleeve by a small distance, as shown. The central hole in the flange 99 of the blocking member is sufficiently large to permit the internally projecting part of the cap 142 to pass therethrough, and the blocking member has an internal abutment 143 spaced rearwardly from the front face of that member.

The initial position of the safety assembly, as supplied for use, is as shown in FIGS. 11A and 11B. It is connected to a syringe body 148 by inserting the forward end of the syringe into the bore 136 of the sleeve 134 and engaging the spigot 149 with the support 128. As the syringe body moves deeper into the sleeve 134, the support 128 is also moved forwardly as shown in FIG. 11C, commencing the engagement of the luer-lock.

This continues until the support 128 abuts the rearward end of the cap 142, within the sleeve 134 (FIG. 11D) and continued pressure on the syringe then fully connects the Luer lock, between the syringe spigot 149 and the support 128 (FIG. 11E). Depending upon the strength of the connection between the cap 142 and the front part 140 of the sleeve, it might be necessary to apply endwise pressure on the cap 142—for example by supporting the forward end of the cap 142 on a hard surface such as a table, and pressing the syringe body downwardly to engage the Luer lock.

Following full engagement of the spigot 149 with the support 128, release of the safety device returns it to its original setting, as shown in FIG. 11F. Then, the cap 142 may be broken away by applying a sideways force thereto (FIG. 11G). During this operation, the needle is withdrawn from the cap and so there is no risk of damage to the sharp end of the needle as the cap is broken away; this can be contrasted with the usual arrangement employed with single-use syringes where great care must be taken to move the cap axially, to avoid catching, and so burring, the sharp end of the needle.

The syringe is filled with an appropriate quantity of medicament by gently pressing a phial 145 on to the flange 90 at the forward end of the sleeve 134, so permitting the syringe and connected needle to move deeper into the safety assembly. The needle penetrates the pierceable membrane 146 of the phial, to permit the extraction of medicament therefrom by withdrawing the syringe plunger. Only light pressure is required to achieve this penetration, and so the lip 100 of the blocking member 131 remains rearwardly of the rib 94 within the front part 140 of the sleeve (FIG. 11H).

Following filling of the syringe, the phial 145 is pulled away from the needle, so allowing return of the safety assembly to its initial setting, though without the cap 142 and so ready for use to perform an injection (FIG. 11J).

From here, the operation of the safety assembly is much as has been described above with reference to the previous embodiments. On performing a stabbing action to effect needle penetration into a body, the sleeve 134 initially moves rearwardly with respect to the support 128, taking the blocking member 131 with it until the support engages the annular abutment 143 within the blocking member 131 (FIG. 11K). Continued rearward movement of the sleeve causes the lip 100 to ride over the rib 94 until maximum projection of the needle is achieved (FIG. 11L), where the front of the blocking member 131 engages the upstand 92 on the flange 90 of the sleeve 134. Finally, after completing the injection and then withdrawing the needle from a body, the sleeve moves forwardly with respect to the syringe body, under the action of the spring 132 bearing on the blocking member. The flange 99 of the blocking member remains in engagement with the flange 90 of the sleeve 134 so that when the sleeve has moved fully forwardly with respect to the syringe and connected support 128, the blocking member is free to cant over and fulfil its blocking function (FIG. 11M).

FIGS. 12A and 12B

FIGS. 12A and 12B show a modified form of the eighth embodiment, of FIG. 9. This modified form has a shorter overall length, achieved by providing a two-part support 155 the outer part 156 of which is folded back on itself in order to provide a surrounding annular space 157 within which the blocking member is slidably received. The rib 94 of the sleeve 117 is correspondingly nearer its flange 90. Thus, in the initial setting, the blocking member is disposed forward of the front end of the support 155 and so the spring is not fully compressed. Further, the distance the blocking member may move before engaging the upstand 92 is much reduced.

In other respects, the construction and operation of this modified form corresponds to that of the eighth embodiment (FIG. 9) and so will not be described in detail again, here.

FIGS. 13A to 13C

FIGS. 13A to 13C illustrate a tenth embodiment of this invention which, while generally similar to that of the eighth embodiment (FIG. 9) differs in one important detail. However, like parts with those of FIGS. 9A to 9E are given like reference numbers.

The embodiment of FIGS. 13A to 13C does not include a rib 94 within the sleeve 89, so that the blocking member is held by spring 98 in a fully forward position, when the assembly is in its initial setting (FIGS. 13A and 13B). However, the blocking member is maintained coaxial with the support 115 and sleeve 117 by means of a slip ring 159, slidably carried but a light frictional fit on the support 115. The rearward end of the blocking member 97 is received within a counter-bore in the slip ring 159.

On performing an injection, the sleeve 117 is moved rearwardly, taking the slip ring 159 with it. Then, following completion of the injection, the sleeve and blocking member move forwardly once more but the slip ring 159 remains in its rearmost position, on the support 115. Thus, on the sleeve and blocking member moving fully forwardly, the blocking member moves to its blocking position as shown in FIG. 13C, thus rendering the assembly safe with the sleeve blocked against movement away from its protecting position.

In all of the above embodiments, the respective sleeves may be made transparent, translucent or provided with a transparent or translucent window. By manufacturing the respective blocking member from a strongly-coloured material, the position of the blocking member within the sleeve will readily be discernible. Then, when the safety device has been used and the blocking member is fully forward, this will immediately be apparent on looking at the assembly.

The invention claimed is:

1. A safety arrangement for a medical needle having a mount end and a sharp tip, which arrangement comprises:
   a support adapted directly or indirectly to carry the mount end of a needle so that the needle has a part projecting forwardly away therefrom;
   a sleeve mounted directly or indirectly on the support and being slideable with respect thereto from an initial position where the sleeve fully covers the projecting part of a carried needle to a retracted position where the tip of a carried needle and a part of the needle back from its tip is exposed, and then to a protecting position corresponding to the initial position and where the sleeve again covers the projecting part of the needle, said protecting position of the sleeve relative to said tip of the needle corresponding to the initial position of the sleeve relative to said tip;
   resilient means arranged to urge the sleeve towards its protecting position;
   a tubular blocking member at least a part of which projects forwardly from the support, the blocking member having a non-blocking position where the blocking member is co-axial with the sleeve whereby the sleeve is slidable with respect to the blocking member to said retracted position, and the blocking member having a blocking position where the axis of the blocking member lies at an acute angle to the sleeve and the blocking member is disposed between the support and a part of the sleeve, thereby blocking movement of the sleeve away from said protecting position; and control means for maintaining the blocking member co-axial with the sleeve during movement of the sleeve from its initial position to its retracted positions, but during movement of the sleeve from its retracted position said control means releases the blocking member for movement to its blocking position, and on subsequent movement of the sleeve to its protecting position the blocking member thereafter blocks movement of the sleeve away from its protecting position.

2. A safety arrangement as claimed in claim 1, wherein one end of the blocking member when in its blocking position co-operates with a wall portion of one of the support and the sleeve to apply a turning moment to the blocking member about an axis transverse to the length of the sleeve, so moving the second end of the blocking member to block retracting movement of the sleeve.

3. A safety arrangement as claimed in claim 2, wherein one end of the blocking member has an off-set boss projecting towards said adjacent wall portion of said one of the support and the sleeve, whereby on the one end of blocking member being urged towards said adjacent wall portion, the off-set projection applies said turning moment to the blocking member.

4. A safety arrangement as claimed in claim 2, wherein said wall portion has an off-set boss projecting towards the adjacent one end of the blocking member, whereby on said one end of the blocking member being urged towards said wall portion, the off-set projection applies said turning moment to the blocking member.

5. A safety arrangement as claimed in claim 2, wherein one end of the blocking member presents a non-radial face to said adjacent wall portion of said one of the support and the sleeve, whereby on the one end of blocking member being urged towards said adjacent wall portion, the non-radial face applies said turning moment to the blocking member.

6. A safety arrangement as claimed in claim 2, wherein said wall portion presents a non-radial face to the adjacent one end of the blocking member, whereby on said one end of the blocking member being urged towards said wall portion, the non-radial face applies said turning moment to the blocking member.

7. A safety arrangement as claimed in claim 1, wherein said support includes a bore in which is receivable a hypodermic syringe having said needle mounted on the forward end thereof such that when the syringe is received within said bore, the needle projects forwardly into the sleeve.

8. A safety arrangement as claimed in claim 7, wherein the sleeve is slidably mounted externally on the support.

9. A safety arrangement as claimed in claim 7, wherein the sleeve is slidably received within a tubular carrier, which carrier is mounted on said support.

10. A safety arrangement as claimed in claim 8, wherein the forward end of the sleeve has a generally radial inwardly directed flange having a central aperture though which the tip of the needle may project when the sleeve is in its withdrawn position.

11. A safety arrangement as claimed in claim 7, wherein the blocking member is slidably carried on the sleeve but slides off the sleeve under the action of the resilient means to move to its blocking position when released by the control means.

12. A safety arrangement as claimed in claim 1 for use with a hypodermic syringe having a cylindrical body provided with a spigot at its forward end for receiving a needle having a mounting hub at its rearward end, wherein said support includes a socket for receiving the spigot of a hypodermic syringe, the support being provided with a needle to project forwardly from a mounted syringe with the needle in communication with the spigot, and the sleeve being slideable on the external surface of the syringe body.

13. A safety arrangement as claimed in claim 12, wherein the support has a greater diameter than the external diameter of the syringe body and the blocking member is slideable over said external diameter of the support.

14. A safety arrangement as claimed in claim 1 for use with an injection device adapted to hold a cartridge of medicament which device has a cylindrical body provided with a spigot at its forward end, wherein said support includes a socket for receiving the spigot of the device, the support being provided with a needle to project forwardly from the spigot with the rear end of the needle in communication with a cartridge carried by the device, the support having an external wall on which the sleeve is slidably supported.

15. A safety arrangement as claimed in claim 12, wherein the support has a forwardly-directed cylindrical surface of a smaller diameter than the external wall on which the sleeve is slideable, the blocking member being slidably carried on said cylindrical surface.

16. A safety arrangement as claimed in claim 1, wherein the control means includes a releasable connection between the sleeve and the blocking member.

17. A safety arrangement as claimed in claim 16, wherein movement of the sleeve towards its retracted position releases the connection to permit the blocking member to move towards its blocking position.

18. A safety arrangement as claimed in claim 17, wherein there is a secondary releasable connection between the sleeve and the blocking member displaced axially from the first-mentioned releasable connection, the secondary releasable connection being released by initial movement of the sleeve towards its withdrawn position, and the first-mentioned releasable connection being released by further movement of the sleeve towards its withdrawn position so freeing the blocking member to move to its blocking position.

19. A safety arrangement as claimed in claim 16, wherein the releasable connection comprises inter-engaged stops respectively on the mutually sliding surfaces of the blocking member and the sleeve, which stops will over-ride each other on the application of a sufficient axial force thereto.

20. A safety arrangement as claimed in claim 1, wherein there is a control member receivable within the sleeve and which initially supports the blocking member to lie substantially coaxial with the sleeve, there being a releasable connection between the sleeve and the control member which when released by movement of the sleeve away from its initial position permits the blocking member to move to its blocking position on movement of the sleeve to its protecting position.

21. A safety arrangement as claimed in claim 20, wherein the control member is located partly within the sleeve and partly within the blocking member, when the sleeve is in its initial position.

22. A safety arrangement as claimed in claim 21, wherein the releasable connection is formed directly between the outer surface of the control member and the internal surface of the sleeve.

23. A safety arrangement as claimed in claim 20, wherein the releasable connection comprises inter-engaged stops on both the outer surface of the control member and the internal surface of the sleeve, which stops will over-ride each other on the application of a sufficient axial force thereto.

24. A safety arrangement as claimed in claim 23, wherein the resilient means acts between the control member and an internal flange formed within the blocking member and so indirectly on the sleeve through the releasable connection.

25. A safety arrangement as claimed in claim 24, wherein the sleeve is formed with an internal stop at its forward end, the control member is a free sliding fit within the sleeve, and when the releasable connection is released, the control member moves forwardly under the action of the resilient means into engagement with the internal stop.

26. A safety arrangement as claimed in claim 20, wherein the releasable connection is formed by the control member fitting in the sleeve in a frictionally-engaging manner.

27. A safety arrangement as claimed in claim 26, wherein the resilient means surrounds the blocking member to act directly between one end of the sleeve and the blocking member.

28. A safety arrangement as claimed in claim 26, wherein the control member includes an axial projection which is received in the blocking member and is withdrawn therefrom by movement of the sleeve towards the needle tip, drawing the control member therewith.

29. A safety arrangement as claimed in claim 28, wherein the length of the axial projection is selected to control the maximum permissible movement of the sleeve towards its retracted position before subsequent movement of the sleeve in the opposite direction locks the sleeve against movement towards a retracted position.

30. A safety arrangement as claimed in claim 20, wherein the support defines a connector for a cylindrical body to extend coaxially with a needle connected thereto.

31. A safety arrangement as claimed in claim 30, wherein a connected cylindrical body serves slidably to support a sleeve moved from its initial position.

32. A safety arrangement as claimed in claim 30, wherein the support is defined by a rear wall of a tubular housing on or within which the sleeve is slidably mounted.

33. A safety arrangement as claimed in claim 1, wherein the resilient means comprises a helical coil spring.

34. A safety arrangement as claimed in claim 1 and in combination with a needle the mount end of which is secured to the support, to project forwardly therefrom.

* * * * *